United States Patent
Corbett et al.

(10) Patent No.: US 11,324,887 B2
(45) Date of Patent: May 10, 2022

(54) REPORTING SYRINGE

(71) Applicants: Jeremy Corbett, Nicholasville, KY (US); John Spencer, Richmond, KY (US); Nathaniel Mitchell, Nicholasville, KY (US)

(72) Inventors: Jeremy Corbett, Nicholasville, KY (US); John Spencer, Richmond, KY (US); Nathaniel Mitchell, Nicholasville, KY (US)

(73) Assignee: DATADOSE, LLC, Lexington, KY (US)

( * ) Notice: Subject to any disclaimer, the term of this patent is extended or adjusted under 35 U.S.C. 154(b) by 139 days.

(21) Appl. No.: 16/131,749

(22) Filed: Sep. 14, 2018

(65) Prior Publication Data

US 2020/0086046 A1   Mar. 19, 2020

(51) Int. Cl.
*A61M 5/172* (2006.01)
*G16H 20/17* (2018.01)
*A61M 5/20* (2006.01)

(52) U.S. Cl.
CPC ............ *A61M 5/172* (2013.01); *G16H 20/17* (2018.01); *A61M 5/20* (2013.01); *A61M 2205/3553* (2013.01); *A61M 2205/50* (2013.01)

(58) Field of Classification Search
CPC ...... A61M 5/20; A61M 5/315; A61M 5/3157; A61M 5/31571
See application file for complete search history.

(56) References Cited

U.S. PATENT DOCUMENTS

| 7,300,418 B2 | 11/2007 | Zaleski |
| 9,623,191 B2 | 4/2017 | Uber |
| 2003/0110060 A1 | 6/2003 | Clementi |
| 2007/0225653 A1* | 9/2007 | Lim ...................... A61B 90/98 604/187 |
| 2015/0174342 A1* | 6/2015 | Mitrosky ............ A61M 5/1684 604/506 |
| 2017/0095638 A1* | 4/2017 | Young ..................... A61M 5/20 |
| 2017/0119969 A1* | 5/2017 | McCullough ......... A61M 5/326 |
| 2017/0146381 A1 | 5/2017 | Eckel |
| 2018/0085517 A1* | 3/2018 | Laurence .............. A61M 5/145 |
| 2018/0193564 A1 | 7/2018 | Dahmani |
| 2018/0369488 A1* | 12/2018 | Carlsson ............. A61M 5/2033 |
| 2019/0054247 A1* | 2/2019 | Dantsker ........... A61M 5/31571 |
| 2019/0282761 A1* | 9/2019 | Wilson .............. A61M 5/31568 |

FOREIGN PATENT DOCUMENTS

| WO | 2016210404 | 12/2016 |
| WO | 2017156523 | 9/2017 |
| WO | 2018009509 | 1/2018 |
| WO | 2018106475 | 6/2018 |

* cited by examiner

*Primary Examiner* — Lauren P Farrar
(74) *Attorney, Agent, or Firm* — JCIP; Jeremy I. Maynard; Joseph G. Chu

(57) ABSTRACT

A reporting syringe, including a barrel in fluid communication with a needle connected with a first end of the barrel, a piston including a plunger, the piston positioned within a second end of the barrel and the plunger having a fluid-tight interaction with an interior of the barrel, and a microprocessor in electronic communication with a switch and a wireless module, the microprocessor configured to send an administration completion data from the wireless module after triggering the switch.

2 Claims, 23 Drawing Sheets

REPORTING SYRINGE

FIELD OF THE INVENTION

The present invention relates generally to syringes and data reporting.

BACKGROUND

Injection is the act of putting a liquid, especially a drug, into a person's body using a needle (usually a hypodermic needle) and a syringe. Injection is a technique for delivering drugs by parenteral administration, that is, administration via a route other than through the digestive tract. Parenteral injection may include subcutaneous, intramuscular, intravenous, intraperitoneal, intracardiac, intraarticular and intracavernous injection.

Injection may be administered as a single dose or bolus, but can possibly be used for continuous drug administration as well. Even when administered as a one-time injection, the medication may be long-acting, and can then be called depot injection. Administration by an indwelling catheter may also be possible in cases of long-term or recurrent drug administration.

Injections may be among the most common health care procedures, with at least 16 billion administered in developing and transitional countries each year. 95% of injections may be administered in curative care, 3% may be for immunization, and the rest for other purposes, such as blood transfusions.

SUMMARY

Aspects of the present invention relate to a reporting syringe, including a barrel in fluid communication with a needle connected with a first end of the barrel, a piston including a plunger, the piston positioned within a second end of the barrel and the plunger having a fluid-tight interaction with an interior of the barrel, and a microprocessor in electronic communication with a switch and a wireless module, the microprocessor configured to send an administration completion data from the wireless module after triggering the switch.

Additional aspects of the invention relate to a syringe, including a barrel in fluid communication with a needle connected with a first end of the barrel, a piston including a plunger, the piston positioned within a second end of the barrel and the plunger having a fluid-tight interaction with an interior of the barrel, and a microprocessor in electronic communication with a temperature sensor and a locking mechanism engaged with a stalk of the piston to prevent injection.

Further aspects of the invention relate to a method of reporting patient compliance, including generating, by a syringe including reporting components, an administration completion data including a binary administration completion flag, and sending the administration completion data.

BRIEF DESCRIPTION OF THE DRAWINGS

Various aspects of the present invention are illustrated by way of example, and not by way of limitation, in the accompanying drawings.

DETAILED DESCRIPTION OF THE PREFERRED EMBODIMENTS

Figure 1A:
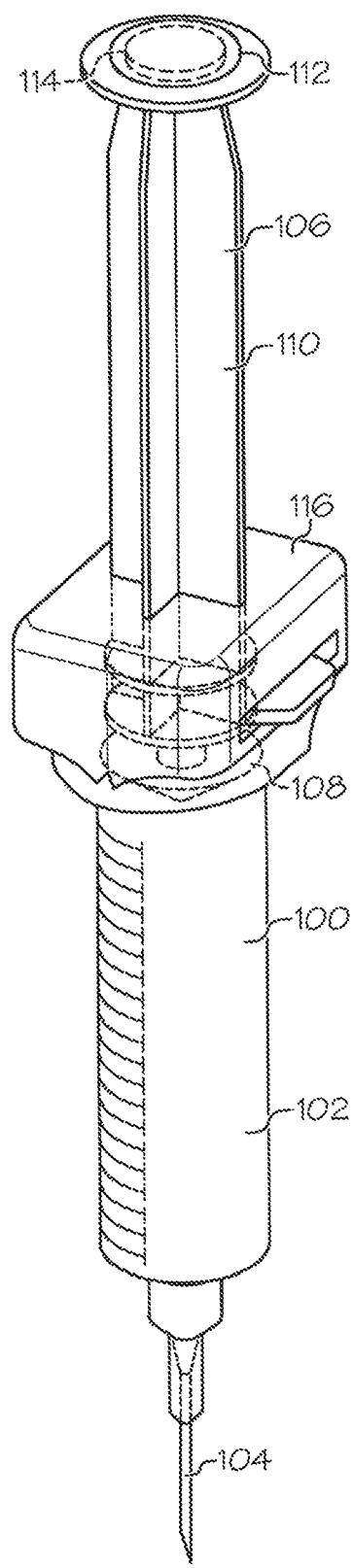
FIG. 1A depicts a diagram of a reporting syringe in accordance with the principles of the present invention.

The present invention relates generally to syringes and, more particularly, to data reporting regarding administration completion of an injectable pharmaceutical.

Injection is the act of putting a liquid, especially a drug, into a person's body using a needle (usually a hypodermic needle) and a syringe. Injection is a technique for delivering drugs by parenteral administration, that is, administration via a route other than through the digestive tract. Parenteral injection may include subcutaneous, intramuscular, intravenous, intraperitoneal, intracardiac, intraarticular and intracavernous injection.

Injection may be administered as a single dose or bolus, but can possibly be used for continuous drug administration as well. Even when administered as a one-time injection, the medication may be long-acting, and can then be called depot injection. Administration by an indwelling catheter may also be possible in cases of long-term or recurrent drug administration.

Injections may be among the most common health care procedures, with at least 16 billion administered in developing and transitional countries each year. 95% of injections may be administered in curative care, 3% may be for immunization, and the rest for other purposes, such as blood transfusions.

An injection may be administered to different depths in different types of injections, including intramuscular, subcutaneous, intravenous, and intradermal (ordered from greatest to least depth). For example, the depth may be gauged by length of needle or angle of injection. Intramuscular injections may be administered at 90 degrees. Subcutaneous injections may be administered at 45 degrees. Intravenous injections may be administered at 25 degrees. Intradermal injections may be administered at 10 to 15 degrees.

Diabetes, among other health issues, may require regular injections for disease management. However, health care providers, insurance providers, and other stakeholders may rely on patient self-reporting for treatment compliance. Furthermore, orphan drugs and limited distribution drugs may have limited availability and/or high cost. Therefore, real-time tracking of patient compliance, as described with respect to the present invention, may be beneficial to physicians to gauge outcomes, for pharmacies to maintain timely drug supply, and for health insurance providers to maintain coverage. For example, Harvoni may be used for seven months as a treatment that may cure Hepatitis C. However, it will be unknown to the doctor, except through patient self-reporting, whether the patient is compliant with treatment. If the patient is compliant and a cure and/or remission is achieved, then the physician knows the treatment was successful. However, if the patient is compliant and cure and/or remission is not achieved, then the physician knows to continue treatment for a longer period or to pursue alternative treatment options. In some instances, patients may have multiple insurance payers, such as Medicare or Medicaid coverage with a supplemental private insurance plan. When this occurs, real-time patient administration completion data may be used to make coverage determinations between the patient and insurers and/or between insurance providers.

Embodiments of the present invention may bring novel biologics compliance to the market for the first time. Insurers, employers, health care providers, and loved ones may benefit when patient care plans receive a monocular focus on quality and completion. Embodiments of the present invention may provide those with acute and chronic conditions in need of regular pharmaceutical therapy, such as an ongoing course of life-saving injectable drugs, with real-time data management related to both timing of and compliance in dosing. Information shared across the care continuum may provide valuable insight into how and when providers should intervene, and may further eliminate fraud, waste, and abuse within this expensive space. Embodiments of the present invention may drive compliance, illuminate opportunities for intervention, and save money in the pharmaceutical space with great need for innovation and within a population that deserves the best care available.

For example, many biologics may have a high cost per injection. Humira, Enbrel, and/or Remicade may be used as an immunosuppressant to treat autoimmunity. These biologics may be expensive. For example, Humira may cost up to $5,000 per injection. Furthermore, the biologics may be temperature sensitive. Humira and Enbrel may be recommended to be stored between 2 and 8 degrees Celsius, without freezing, and may be kept at room temperature for up to 14 days. Such a temperature range corresponding to the temperature tolerance of a pharmaceutical may be referred to as a predetermined temperature range. The time period that a pharmaceutical may exceed the predetermined temperature range may be referred to as a time tolerance. Regarding some pharmaceuticals, such as biologics, the time tolerance may exclude freezing. Remicade may be recommended to be stored between 2 and 8 degrees Celsius, without freezing, and may be kept at room temperature for 24 hours. Due to the sensitivity of these biologics, a pharmacist may refuse inventory shipments wherein cold chain storage has been broken. These biologics may be shipped preloaded into syringes.

The detailed description set forth below in connection with the appended drawings is intended as a description of various embodiments of the invention and is not intended to represent the only embodiments in which the invention may be practiced. The detailed description includes specific details for the purpose of providing a thorough understanding of the invention. However, it will be apparent to those skilled in the art that the invention may be practiced without these specific details. In some instances, well known structures and components are shown in block diagram form in order to avoid obscuring the concepts of the invention.

As used herein, "near" means within ⅓ of the area of the container unit. For example, if a portion of a first structure is described as "near" a second structure, the first structure is within ⅓ of the length of the container unit from the second structure.

As used herein, "about" means within plus or minus one at the last reported digit. For example, about 1.00 means 1.00±0.01 unit. In fractions, about 1 1/16 units means from 1 0/16 units to 1 2/16 units. In percentages, about 11% means 10% to 12%.

As used herein, "Id" refers to a unique identifier corresponding to a real-world counterpart. For example, patient Id refers to a unique identifier corresponding to a patient. The unique identifier may be used to associate other data to the counterpart, such as the patient, by association of the Id. Furthermore, the Id may be used in electronic storage, such as a unique key to distinguish patients and patient-related information in a database.

With respect to the present application, "around" used in conjunction with a numeral measurement means within plus or minus one unit. For example, around 50% means 49%-51%. For example, around 11.01 units means 10.01-12.01.

With respect to the present application "and" and "or" shall be construed as conjunctively or disjunctively, whichever provides the broadest disclosure in each instance of the use of "and" or "or."

"Substantially," as used herein with reference to a shape, means within manufacturing tolerance of manufacturing the referenced shape as well as any other shape falling within the doctrine of equivalents for the referenced shape.

Any directional words, such as "top," "bottom," "up," "down," etc. used herein refer to the direction depicted in the figure described. If the described device is rotated, these directions remain indicative of the position described relative to the figure.

"Connected to," as used herein, means a direct physical connection between structures without intervening structures.

"Connected with," as used herein, means a physical connection between structures, with or without intervening structures.

"Administration completion," as used herein, means a complete or substantially complete administration of a pharmaceutical from a syringe. A "substantially complete administration" of a pharmaceutical means that injection has been administered such that a switch of reporting components is triggered to correspond with administration completion.

FIG. 1A depicts a diagram of a syringe 100 in accordance with the principles of the present invention. Syringe 100 may include a barrel 102. The barrel 102 may be sized to receive and/or store a pharmaceutical, such as a medication, a biologic, etc. With respect to diabetes management, the barrel 102 may be sized to retain sufficient insulin for one prescribed administration. The pharmaceutical may be injected into a patient, such as via needle 104. The needle 104 may comprise a hollow conduit through which the pharmaceutical may be transported from barrel 102 through needle 104 and into the patient.

Injection may be driven by a piston 106. Piston 106 may comprise a plunger 108, a stalk 110, and a head 112. The plunger 108 may engage the inside of the barrel 102 such that a seal is created sufficient to push retained pharmaceutical from the barrel 102 through the needle 104. The plunger 108 may be connected to the stalk 110. The stalk 110 may be connected to the head 112. The plunger 108 may be driven through the barrel 102 by operation of pressing the head 112 toward the barrel. The plunger may comprise rubber, plastic, or any other material sufficient to maintain a fluid-tight interaction between the plunger 108 and an interior of the barrel 102 such that the pharmaceutical is administered as the piston 106 is compressed. The stalk 110 may have sufficient length to drive the plunger 108 to a distal end of the barrel 102. In this manner, most or all of the pharmaceutical may be driven out of the barrel 102.

In some embodiments, the head 112 may comprise a magnet 114. The magnet 114 may comprise a neodymium or other magnet sufficient to induce its magnetic field onto reporting components 116 when the head 112 is completely pressed to the casing of the reporting components 116. When the magnetic field is induced onto the reporting components 116, the reporting components 116 may send an administration completion data to a server over an internet connection (e.g. wireless, cellular data, etc). In some embodiments, the magnetic field may be induced onto the reporting components 116 when the head 112 is almost completely pressed to the casing of the reporting components 116, such as when the injection administration is effectively complete (e.g. when the head 112 is 98% compressed).

Alternatively, a mechanical switch may be used to indicate that the injection has been administered by compressing the switch when the head 112 is completely pressed to the casing of the reporting components 116 or to an end of the barrel 102. In these embodiments, a reporting circuit may be completed or broken. Detection of this change in the circuit may allow for reporting components 116 (e.g. a microprocessor) to alter an administration completion data to reflect a completed injection.

Figure 1B:
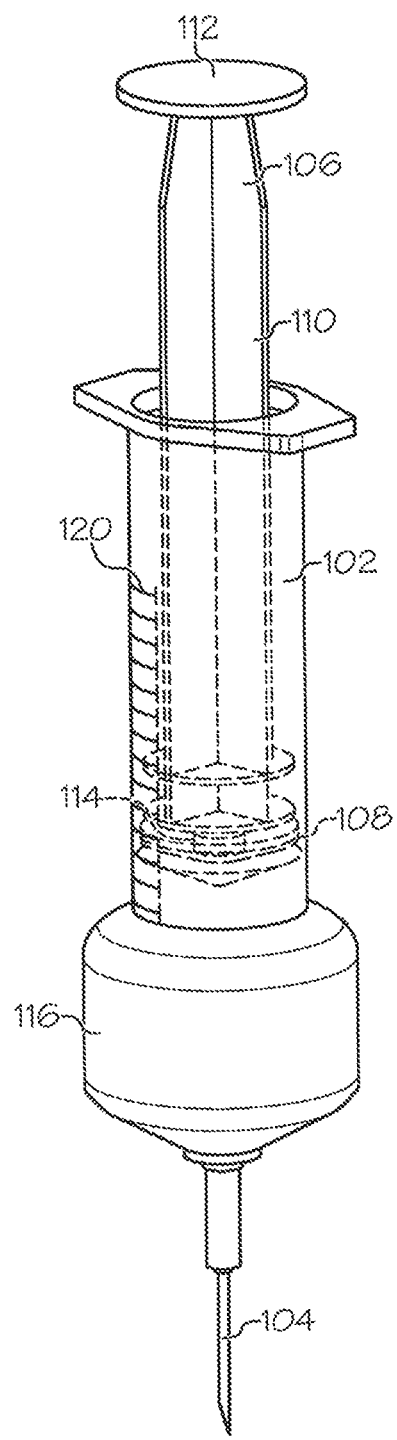
FIG. 1B depicts a diagram of a reporting syringe of having an alternate arrangement of reporting components in accordance with the principles of the present invention.

FIG. 1B depicts a diagram of a reporting syringe 120 having an alternate arrangement of reporting components 116 in accordance with the principles of the present invention. As can be seen, the magnet 114 may be positioned in the plunger 108. The reporting components 116 may be positioned at the end of the barrel 102 proximate the needle 104.

Figure 2A:
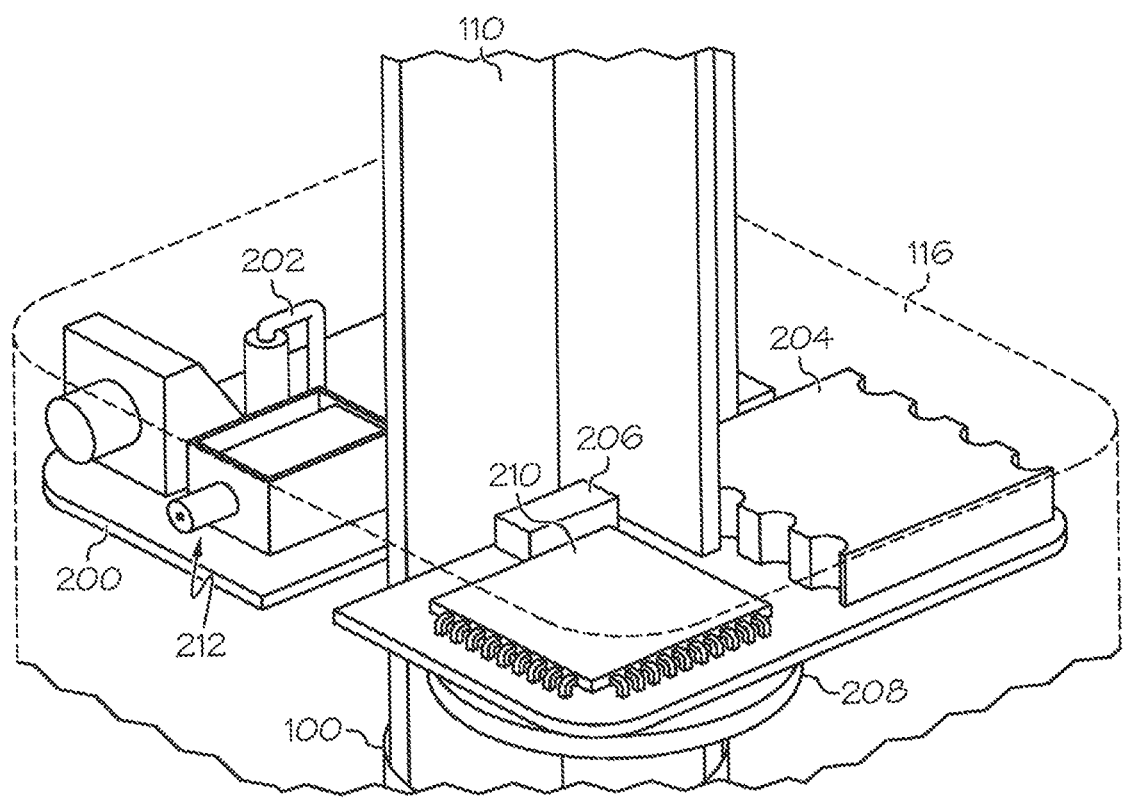
FIG. 2A illustrates reporting components of the syringe of FIG. 1A in accordance with the principles of the present invention.

FIG. 2A illustrates reporting components 116 of the syringe 100 of FIG. 1A in accordance with the principles of the present invention. For example, reporting components 116 may comprise a temperature sensor 202, a wireless module 204, a switch 206, a battery 208, a microprocessor 210, and/or a locking mechanism 212.

The battery 208 may comprise a coin cell battery or any other battery sufficient to power the reporting components 116. Coin cell batteries may provide stable output voltage until the end of life of the battery. Coin cell battery capacities may range from 150 to 200 mAh and voltage characteristics may range from gradually reducing to fairly constant. Some coin cell batteries may be specified for continuous low drain with high pulse on demand.

The temperature sensor 202 may comprise any device for measuring temperature and providing an electronic measurement to the microprocessor 210. Examples include a thermistor, a resistance temperature detector, a thermocouple, and/or a semiconductor-based sensor. In some embodiments, the temperature sensor 202 may be positioned on a circuit board of the reporting components 116. The temperature sensor 202 may be configured to measure the temperature ambient to the syringe 100, such as by measuring the temperature of the air around the reporting components 116. However, embodiments may include a temperature probe within the barrel 102 in order to measure the temperature of the pharmaceutical.

A thermistor may comprise a thermally sensitive resistor that may exhibit a large, predictable, and precise change in resistance correlated to variations in temperature. A negative temperature coefficient (NTC) thermistor provides a very high resistance at low temperatures. As temperature increases, the resistance may decrease. Because an NTC thermistor may experience a large change in resistance per ° C., small changes in temperature may be reflected quickly and with high accuracy (0.05 to 1.5° C.). Because of its exponential nature, the output of an NTC thermistor may require linearization. The effective operating range may be −50 to 250° C. for gas encapsulated thermistors or 150° C. for standard.

A Resistance temperature detector (RTD), also known as a resistance thermometer, may measure temperature by correlating the resistance of the RTD element with temperature. An RTD may consists of a film or, for greater accuracy, a wire wrapped around a ceramic or glass core. The most accurate RTDs may be made using platinum. However, lower cost RTDs can be made from nickel or copper, at a cost to accuracy. Platinum RTDs offer a fairly linear output that may be highly accurate (0.1 to 1° C.) across −200 to 600° C.

A thermocouple may consist of two wires of different metals connected at two points. The varying voltage between these two points may reflect proportional changes in temperature. Thermocouple may be non-linear, requiring conversion when used for temperature control and compensation. However, conversion can be accomplished using a lookup table. Accuracy may be relatively low, from 0.5 to 5° C. However, thermocouples may operate across the widest temperature range, from −200 to 1750° C.

A semiconductor-based temperature sensor may be placed on an integrated circuit (IC). These sensors may comprise two identical diodes with temperature-sensitive voltage vs current characteristics that can be used to monitor changes in temperature. They may offer a linear response but may have the lowest accuracy of the basic sensor types at 1 to 5° C. They may have the slowest responsiveness (5 to 60 s) across the narrowest temperature range (−70 to 150° C.).

The wireless module 204 may be place on the circuit board 200 such that the wireless module 204 may be in electrical communication with the microprocessor 210 and the battery 208. The wireless module 204 may comprise a Bluetooth interface, a Bluetooth low energy interface, a Wi-Fi interface, an infrared interface, a cellular interface (e.g. a fixed area transceiver), a near field communication (NFC) interface, a radio-frequency identification (RFID) interface, etc.

Wireless module 204 may connect to the internet, a computer, and/or a mobile phone. For example, the wireless module 204 may connect directly or indirectly to a local router, modem, server, transmitter tower such as a radio tower, satellite and/or any other gateway to the worldwide web. In some embodiments, the wireless module 204 may be wirelessly connected directly to another computer or handheld device, such as a phone, watch, or tablet. In other embodiments, wireless module 204 may engage in electronic communication with another computer or device by infrared (IR) transmitter and receiver, Bluetooth connection, fiber optic connection, cellular or mobile network (e.g. fixed area transceivers), or any other connector for transferring electronic data. For example, the wireless module 204 may send data over Bluetooth connection to a computer, server, or other device. The server may then upload the data for access via internet connection. Wireless module 204 may transmit data via analog or digital signal, UDP or TCP, http, https, ssh, ftp, sftp, etc., or any other protocol or means to transfer electronic data.

The switch 206 may comprise a magnetic and/or electrical switch, such as a reed switch. The switch 206 may be positioned on the circuit board 200. The switch 206 may be in electrical communication with the microprocessor 210, the locking mechanism 212, and/or any other reporting components 116. A reed switch may be operated by an applied magnetic field. The reed switch may comprise a pair of contacts on ferromagnetic metal reeds in a hermetically sealed glass envelope. The contacts may be normally open, closing when a magnetic field is present, or normally closed and opening when a magnetic field is applied. The reed switch may be actuated by a coil, making a reed relay, or by bringing a magnet near to the switch. Once the magnet is pulled away from the switch, the reed switch may go back to its original position. In this manner, the switch 206 may be actuated by application of the magnetic field of magnet 114, such as when the piston 106 is compressed upon administering an injection or bolus of a pharmaceutical from the barrel 102.

The locking mechanism 212 may be positioned on the circuit board 200. In this manner, the locking mechanism 212 may be in electrical communication with the other components on the circuit board 200, such as the wireless module 204 and/or the microprocessor 210. The locking mechanism 212 may prevent injection of the pharmaceutical by interaction with the stalk 110, when in the locked position. However, the locking mechanism 212 may be switched to an unlocked position, wherein the locking mechanism 212 no longer interact with the stalk 110. Thereby, the piston 106 may be compressable to allow an injection when the locking mechanism 212 is in the unlocked position.

In some embodiments, the locking mechanism 212 may engage the locked position upon filling the barrel with a prescribed amount or bolus of a pharmaceutical. The locking mechanism 212 may remain in the locked position until predetermined conditions are met. For example, the locking mechanism 212 may remain in the locked position until the microprocessor 210 verifies a user connection between the wireless module 204 and a user device, such as an app on a mobile device. In some embodiments, the locking mechanism 212 may switch to the unlocked position upon meeting one or more, or all, of the predetermined conditions.

An example may include sensing that an injection physically occurs within a patient, such as by a load sensor. The load sensor will be explained further with respect to FIGS. 9A-9C.

The microprocessor 210 may be positioned on the circuit board 200. In this manner, microprocessor 210 may be in electrical communication with the other components on the circuit board 200, such as the temperature sensor 202, the wireless module 204, the switch 206, the battery 208, and/or the locking mechanism 212. The microprocessor 210 will be described further with regard to FIG. 3.

Figure 2B:
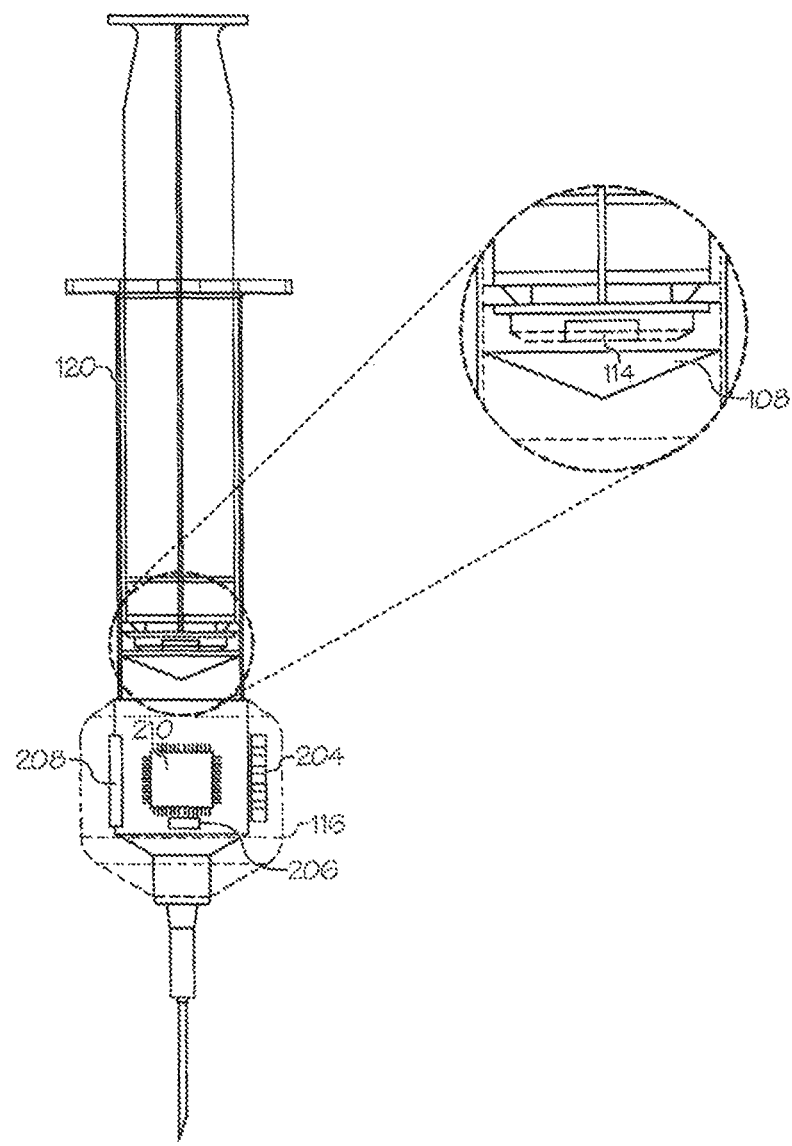
FIG. 2B depicts the reporting components of the reporting syringe of FIG. 1B in accordance with the principles of the present invention.

FIG. 2B depicts the reporting components 116 of the reporting syringe 120 of FIG. 1B in accordance with the principles of the present invention.

Figure 2C:
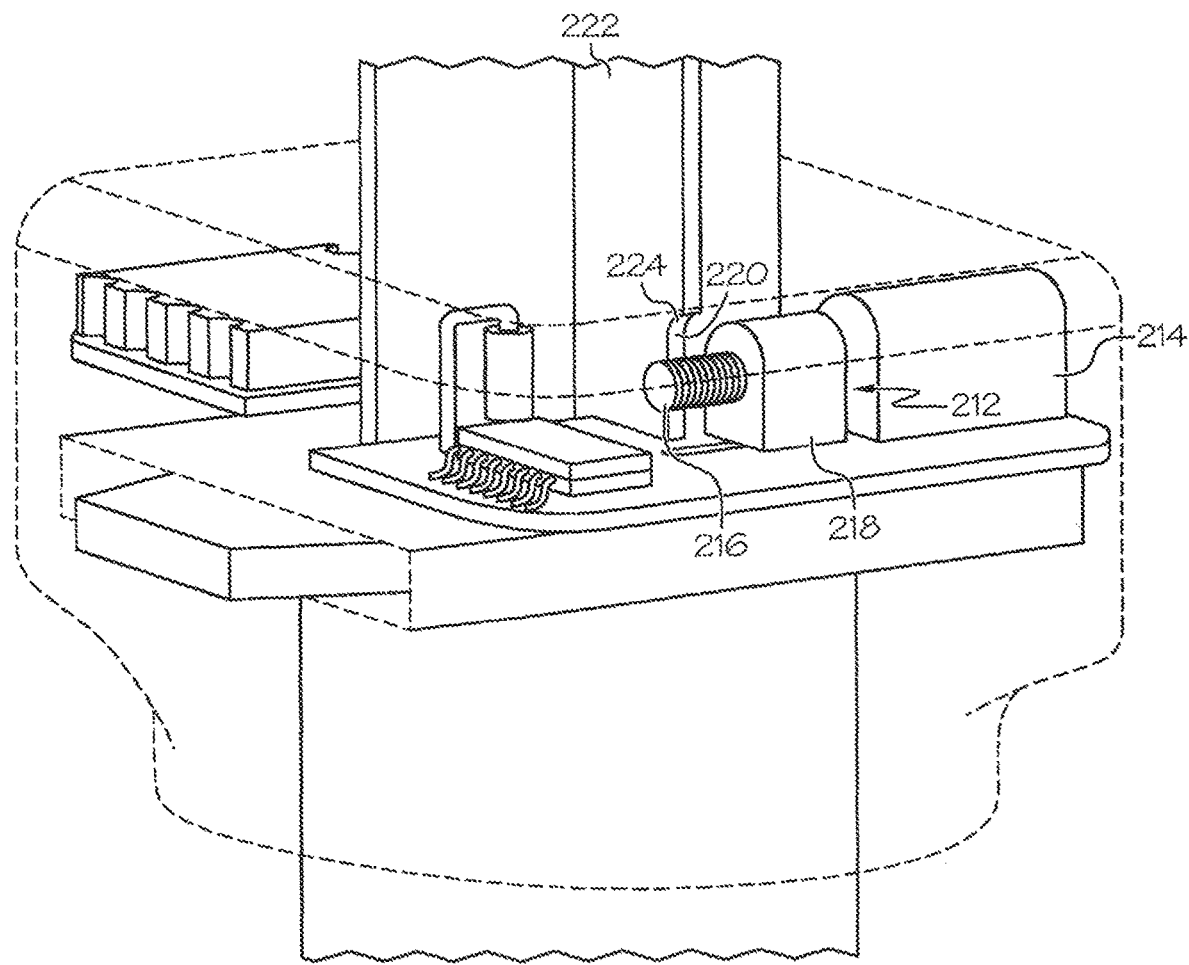
FIG. 2C depicts a locking mechanism of the reporting components of the reporting syringe of FIG. 1A with the locking mechanism disengaged in accordance with the principles of the present invention.

FIG. 2C depicts the locking mechanism 212 of the reporting components 116 of the reporting syringe 120 of FIG. 1A with the locking mechanism 212 disengaged in accordance with the principles of the present invention.

The locking mechanism 212 may comprise a stepper motor, such as micro stepper motor 214. The micro stepper motor 214 may be in rotary communication with a screw 216 such that rotation of the micro stepper motor 214 may rotate screw 216. Slider block 218 may be disposed on screw 216 such that rotation of the screw 216 may alter the linear displacement of the slider block 218. For example, slider block 218 may comprise threads that interact with the threads of screw 216. Therefore, rotation of screw 216 in a first direction may move the slider block 218 proximally to the micro stepper motor 214. Furthermore, rotation of the screw in a second direction may move the slider block 218 distally from the micro stepper motor 214.

The locking mechanism 212 may further comprise a slider block receiver 220. The slider block receiver 220 may be integrally formed with the plunger such that plunger wall 222 comprises a flange 224 configured to contact the slider block 218 when the slider block 218 is positioned under the flange 224. However, the flange 224 may not necessarily contact anything when the slider block 218 is not positioned under the flange 224. In this manner, the wall 222 may pass the slider block 218 and the syringe 100 may be compressed.

Figure 2D:
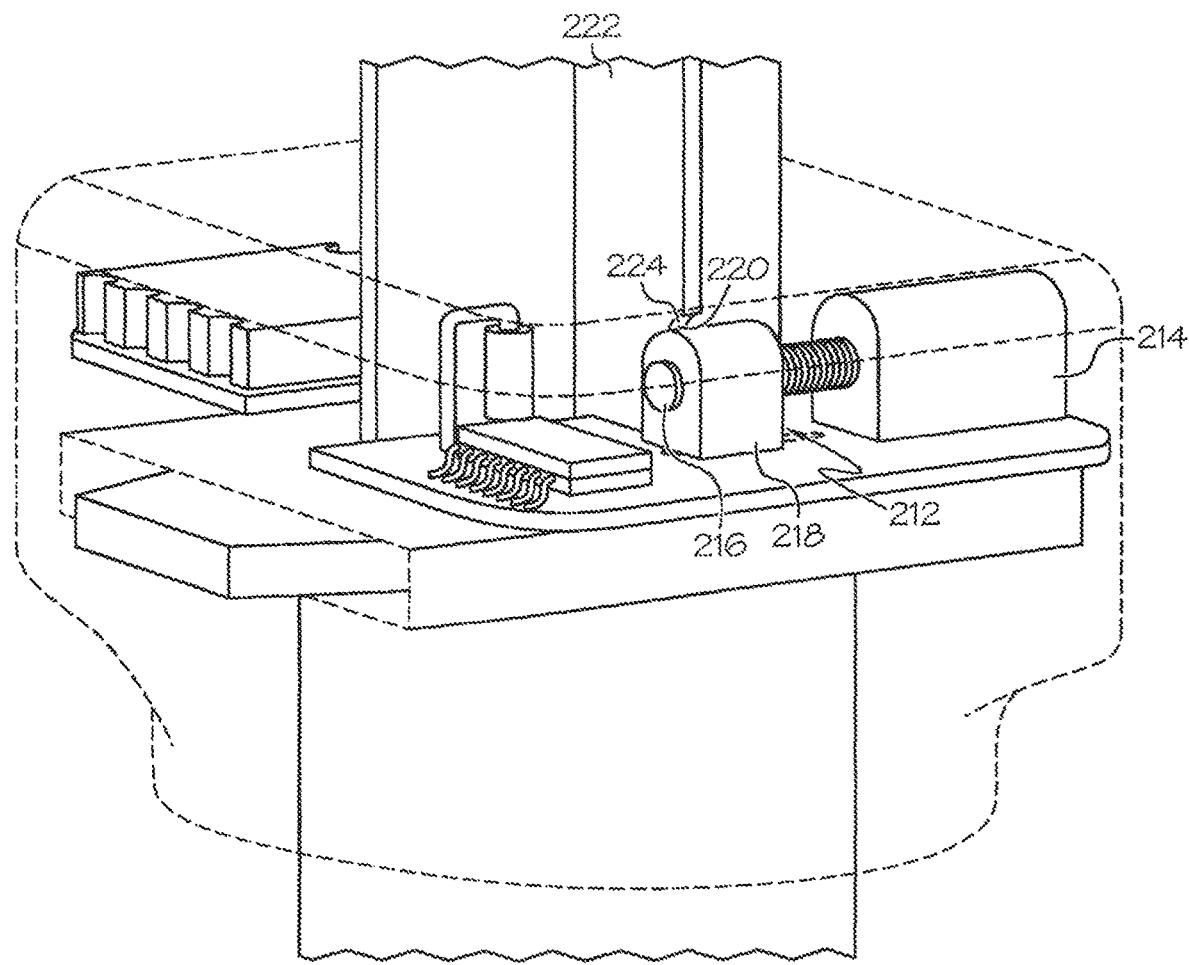
FIG. 2D depicts the locking mechanism of the reporting components of the reporting syringe of FIG. 1A with the locking mechanism engaged in accordance with the principles of the present invention.

FIG. 2D depicts the locking mechanism 212 of the reporting components 116 of the reporting syringe 120 of FIG. 1A with the locking mechanism 212 engaged in accordance with the principles of the present invention. In this manner, flange 224 may contact the slider block 218. Because the flange 224 and/or the wall 222 will not pass through the slider block 218, the syringe 100 will be prevented from compression and/or injection.

The mechanism of locking and/or unlocking may be made possible by the disposition of the axis of the screw 216 through the plane of the wall 222 such that flange 224 is not capable of contacting screw 216 and is capable of contacting slider block 218 when the slider block 218 is positioned under the flange 224. In some embodiments, a mortise of the wall 222 may comprise flange 224 that may contact the slider block 218 (e.g. as a tenon) to prevent injection when the slider block 218 is positioned in the mortise.

One of ordinary skill may recognize alternative locking mechanisms.

Figure 2E:
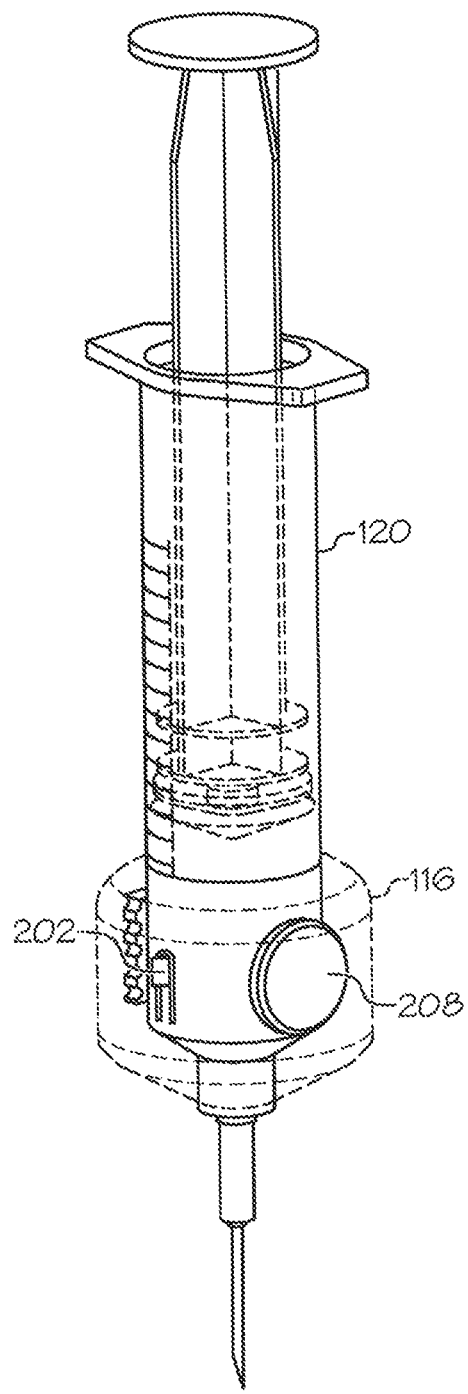
FIG. 2E depicts an alternate view of the reporting components of FIG. 2B in accordance with the principles of the present invention.

FIG. 2E depicts an alternate view of the reporting components 116 of FIG. 2B in accordance with the principles of the present invention. Embodiments of the syringe 120 include reporting components 116 that do not necessarily include a locking mechanism 212. The alternate arrangement syringe 120 depict in FIGS. 1B, 2B, and 2C may be similar in all other respects to the syringe 100 of FIG. 1A. Thus, the switch 202 may detect proximity of the magnet 114 in the plunger 108, when an injection is completely administered. The microprocessor 210 may record the injection administration completion event and may send the administration completion data over the wireless module 204.

Figure 3:
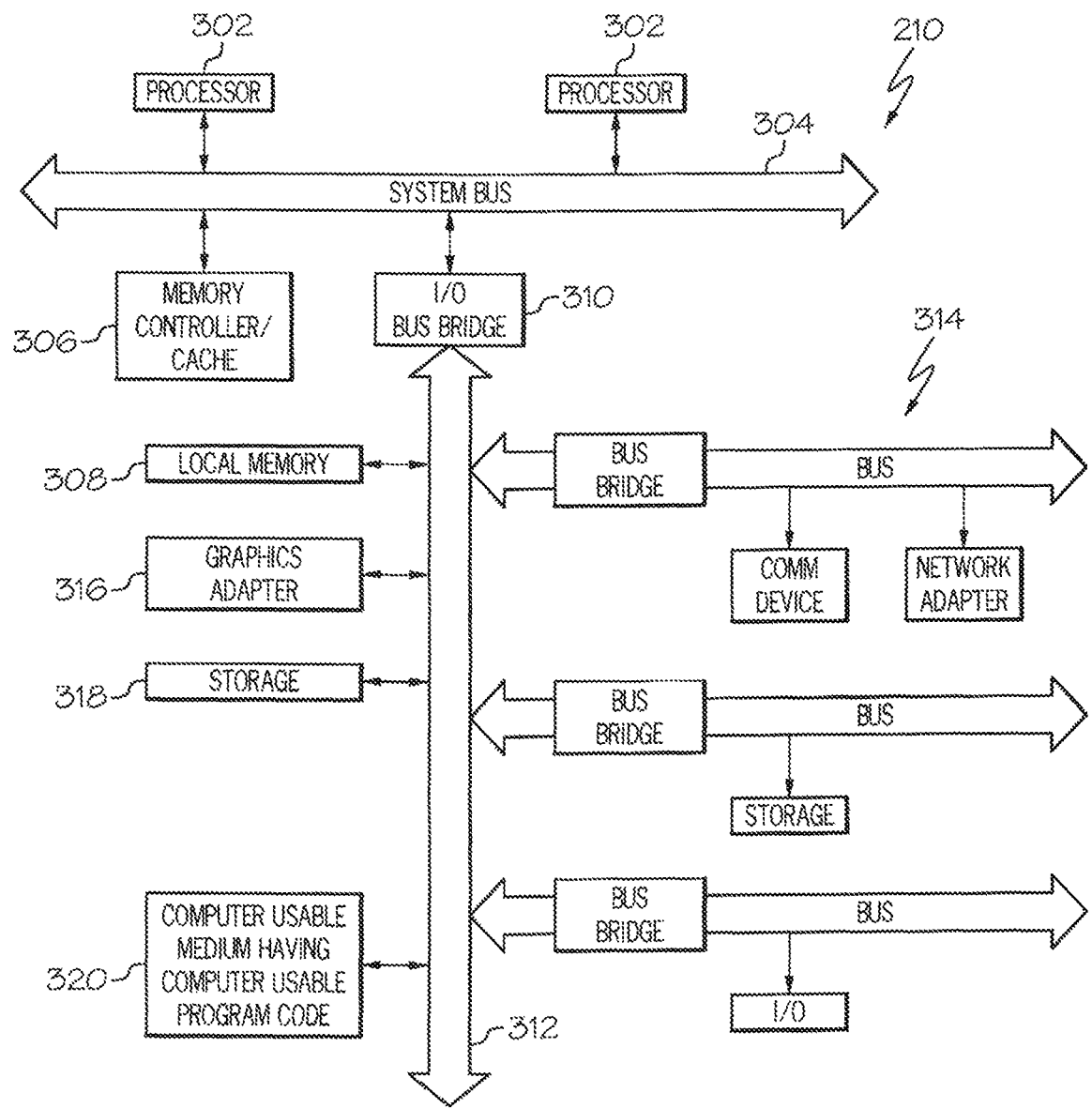
FIG. 3 depicts a diagram of a microprocessor of the syringe of FIG. 1A in accordance with the principles of the present invention.

FIG. 3 depicts a block-level diagram of a microprocessor 210 of the syringe 100 of FIG. 1A in accordance with the principles of the present invention. The microprocessor 210 may be any device capable of sending and receiving electronic data over an interface. For example, a microprocessor or a computer could be used. The microprocessor 210 may also perform operations on and/or modify the data it receives.

The microprocessor 210 may be embodied as hardware circuits or may be software embodiments wherein program code, such as java, C++, etc., manipulates the hardware of a general purpose hardware circuit. Software embodiments may be implemented as low-level code or even as high level code operating within an operating system, such as Unix, BSD, Microsoft Windows, iOS, etc.

Microprocessor 210 may comprise a processing unit (CPU) 302, local memory 308, peripherals and interfaces, and a general purpose input/output (I/O) interface. The CPU may further comprise local storage. Local storage may be used to store variables, constants, etc. for complex calculations. Local memory may interface with the CPU via a memory interface. The memory interface may allow the CPU to store calculated values, variables, constants, or any other important electronic signal onto the physical local memory. The memory interface may include one or more direct memory access controllers. Of course, part or all of the local memory may be committed to program storage, in which data relevant to the operation of the program is stored. Program storage may also be organized into useful data structures such as a stack or heap. The peripherals and interface and the general purpose I/O interface may interface to external input or output devices. Examples of external input or output devices include any electronic device capable of sending or receiving an electronic signal such as keyboards, mice, printers, scanners, digital sensor, analog sensors, Ethernet, analog to digital converters, ADC, UART, USB etc. Program storage, local memory, peripherals and interface, and general purpose I/O interface may be contained on the circuit board of the CPU. The microprocessor 210 may further comprise a screen whereby the graphics adapter 616 may alter the display, such as at validation or denial of a ticket. In other embodiments, any of these parts may be external to the CPU.

Microprocessor 210 may comprise a symmetric multiprocessor (SMP) system or other configuration including a plurality of processors 302 connected to system bus 304. Alternatively, a single processor 302 may be employed. Also connected to system bus 304 is memory controller/cache 306, which may provide an interface to local memory 308. An I/O bridge 310 may be connected to the system bus 304 and may provide an interface to an I/O bus 314. The I/O bus 312 may be utilized to support one or more buses and corresponding devices, such as bus bridges, input output devices (I/O devices), storage, network adapters, etc. Thus, a network adapter may be coupled to the system to enable the data processing system to become coupled to other data processing systems or remote printers or storage devices through intervening private or public networks.

Also connected to the I/O bus 312 may be devices such as a graphics adapter 316, storage 318 and a computer usable storage medium 320 having computer usable program code embodied thereon. The computer usable program code may be executed, e.g., by the processor(s) to implement any aspect of the present invention, for example, to implement any aspect of any of the methods, processes and/or system components with respect to the present invention. For instance, the computer usable program code can be utilized to implement a linker that implements any one or more of the methods described herein. Moreover, the computer usable program code may be implemented in the local memory 308 or other suitable storage medium.

In some embodiments, the reporting components 116 may comprise an attachable and/or detachable self-contained unit. In these embodiments, the reporting components 116 may comprise a case that is shaped to snap fit over the piston-receiving end of the syringe 100. Furthermore, sensors, such as the temperature sensor 202, may detect the ambient temperature of the reporting components 116 as an approximation of temperature of the pharmaceutical in the barrel 102.

Figure 4:
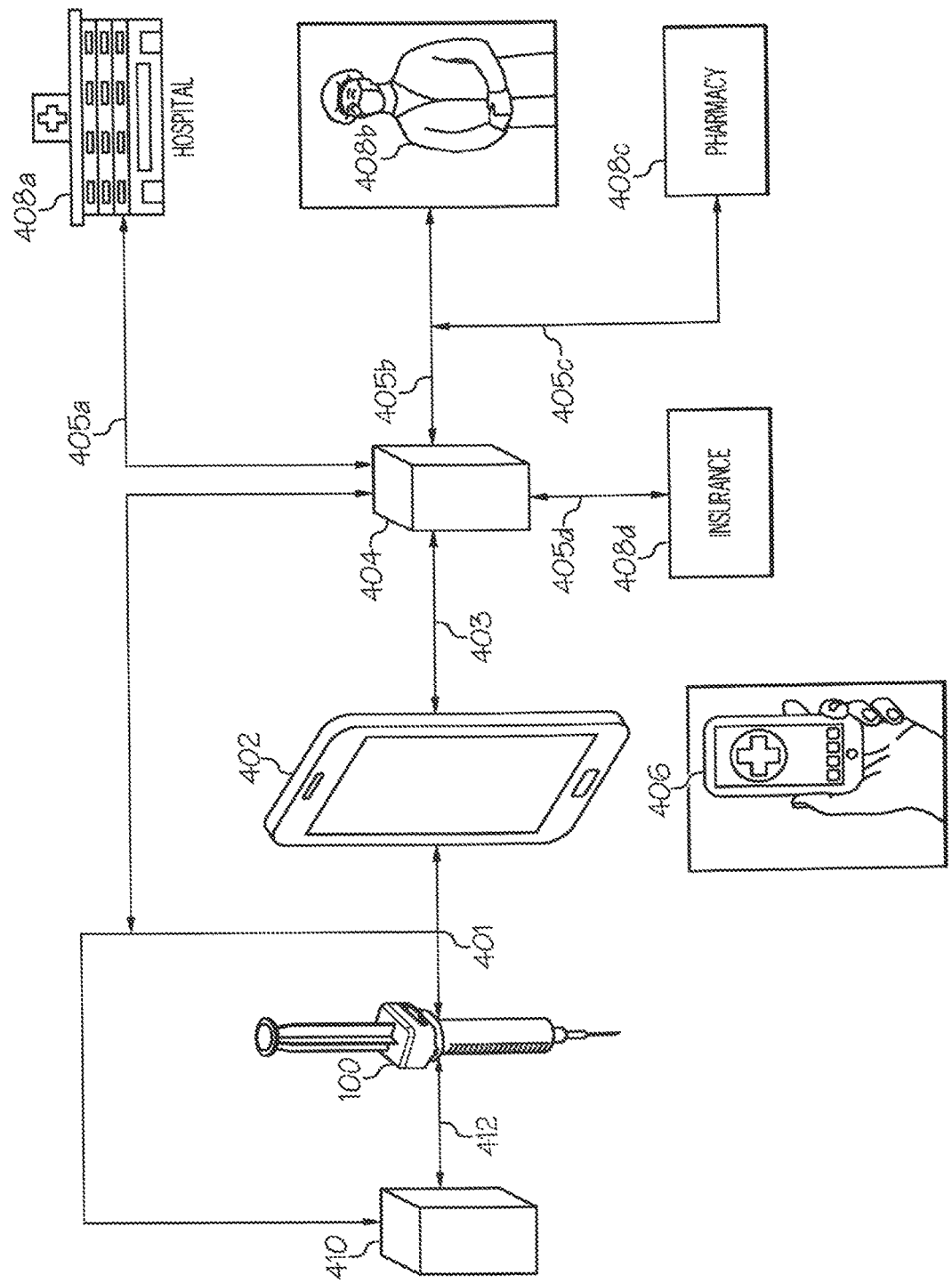
FIG. 4 depicts a diagram of data generation by the syringe of FIG. 1A and data sharing in accordance with the principles of the present invention

FIG. 4 depicts a diagram of data generation by the syringe 100 of FIG. 1A and data sharing in accordance with the principles of the present invention. A processor and/or microprocessor of a patient device 402 and/or a server 404 may be substantially similar to the microprocessor 210 such that patient device 402 and/or server 404 may be programmable to carry out the processes described in accordance with the principles of the present invention.

Internet connection, such as wireless connection 401, internet connection 403, and/or internet connection 405a-405d, may be established via internet connection hardware such as a circuit configured as a wired or wireless internet adapter or other means of electronic communication. In some embodiments, wireless connection 401 may connect the syringe 100 to the patient device 402 over wireless interface 204, as described above.

For example, the internet connections 403 and 405a-405d may be substantially similar to wireless connection 401. In some embodiments, internet connections 403 and 405a-405d may comprise an Ethernet jack for wired connection directly or indirectly to a local router, modem, server, transmitter tower such as a radio tower, satellite and/or any other gateway to the worldwide web. In other embodiments, the internet connections 403 and 405a-405d may comprise a wireless card or circuit. The wireless card may be wirelessly connection directly or indirectly to a local router, modem, server, transmitter tower such as a radio tower, satellite and/or any other gateway to the worldwide web. In some embodiments, the internet connections 403 and 405a-405d may be wirelessly connected directly to another computer or handheld device, such as a phone, watch, or tablet. In other embodiments, internet connections 403 and 405a-405d may engage in electronic communication with another computer or device by infrared (IR) transmitter and receiver, Bluetooth connection, fiber optic connection, cellular or mobile network (e.g. fixed area transceivers), or any other connector for transferring electronic data. For example, the internet connections 403 and 405a-405d may send data over Bluetooth connection to a computer, server, or other device. The server may then upload the data for access via internet connections 403 and 405a-405d. Additional embodiments include an internet connections 403 and 405a-405d that is configured to send the store data over Bluetooth, infrared communication, etc. directly to the server 404. Internet connections 403 and 405a-405d may transmit data via analog or digital signal, UDP or TCP, http, https, ssh, ftp, sftp, etc., or any other means to transfer electronic data.

Internet connection 403 may provide for electronic communication between patient device 402 and server 404. Internet connection 405b may provide for electronic communication between server 404 and a health care stakeholder, such as a physician 408b. Internet connection 405c may provide for electronic communication between server 404 and a health care stakeholder, such as a pharmacy 408c. Internet connection 405d may provide for electronic communication between server 404 and a health care stakeholder, such as an insurance provider 405d.

In some embodiments, patient device 402 may comprise app 406. The app 406 may manage wireless connection 401 and electronic communications between syringe 100 and patient device 402. For example, the app 406 may be registered to a patient, such that the patient may be verified. Patient verification may be provided through a password protected login system and/or a digital certificate system. Once verified, the patient may review treatment data stored by the server 404 by communication between the patient device 402 and the server 404 over internet connection 403. Treatment data may comprise treatment history, and may include patient compliance data.

Furthermore, verification of the patient may unlock the locking mechanism 212 in the syringe 100, such that a may be administered. In some embodiments, the syringe 100 may be preregistered to a patient, such as by a pharmacy 408c that fills the prescription for the drug in the syringe 100. In these embodiments, the app 406 may provide patient verification data to the microprocessor 210. The microprocessor 210 may unlock the locking mechanism 212 upon patient verification. However, the present invention may include embodiments wherein the syringe 100 may not necessarily be preregistered to a patient. In these embodiments, the app 406 may provide patient information, such as a patient Id, or the app 406 may record syringe information, such as a syringe Id. The app 406 may signal that injection may proceed, and the microprocessor 210 may unlock the locking mechanism 212.

In some embodiments, wireless connection 401 may establish electronic communication between the syringe 100 and the patient device 402. The syringe 100 may send administration completion data to the patient device 402 over wireless connection 401. Wireless connection 401 may establish electronic communication between the syringe 100 and the server 404. The syringe 100 may send administration completion data to the server 404 over wireless connection 401.

Furthermore, health care stakeholders 408a-408d may access server 404 to review treatment data stored on the server 404 for corresponding patients. In this manner, stakeholders 408a-408d may make treatment and/or coverage decisions. For example, a provider (e.g. a hospital 408a or a physician 408b) may guide a non-compliant patient towards compliance in order to achieve better treatment outcomes. Additionally, if the desired treatment outcome is not achieved by compliance, alternative treatments may be chosen. Insurance provider(s) 408d may incentivize compliance through allowable avenues or vehicles, such as with additional coverage and/or lower premiums. However, insurance provider 408d may intervene when non-compliance occurs, such as by withdrawing coverage for treatments wherein the patient is non-compliant. Pharmacy stakeholders 408c may compare treatment data to prescriptions in order to provide for timely refills available to encourage patient compliance and also to assess for compliance with a treatment regimen. This process may encourage compliance of proper administration of prescribed pharmaceuticals.

Figure 5:
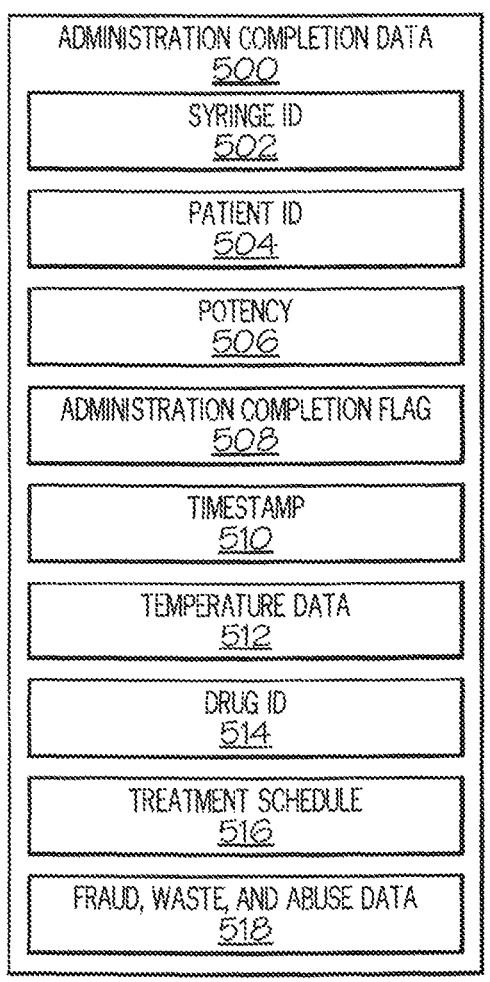
FIG. 5 depicts a block-level diagram of an administration completion data as can stored on the syringe of FIG. 1A in accordance with the principles of the present invention.

FIG. 5 depicts a block-level diagram of administration completion data 500 as can stored on the syringe 100 of FIG. 1A in accordance with the principles of the present invention.

The administration completion data 500 may comprise the syringe Id 502. The syringe Id 502 can be associated with manufacturing lot of the syringe 100 or of a contained pharmaceutical. Furthermore, the administration completion data 500 may comprise a drug Id 514 of the contained pharmaceutical for identifying the drug and/or manufacturing lot of the drug.

The administration completion data 500 may further comprise the patient Id 504. The patient Id 504 may be set by the pharmacy 408c or by the app 406. The potency 506 may comprise the volume and/or concentration of the entire amount of the injectable drug contained in the syringe. The administration completion flag 508 may comprise a binary indicated of whether the injection was completely administered, as detected by the syringe 100. Upon completion of injection administration, the administration completion flag 508 may be changed from False to True. Furthermore, upon completion of injection administration the administration completion data 500 may be sent to the patient device 402 and/or the server 404. In some embodiments, the administration completion data 500 may comprise a treatment schedule 516. When an injection is missed, the syringe 100 may send administration completion data 500 to the patient device 402 and/or the server 404 reflecting a missed injection (e.g. administration completion flag 508 set to False). Further embodiments include sending the administration completion data 500 indicating an incomplete administration when administration is started, but not completed. For example, if a load sensor indicated that an injection was not performed, or if a partial administration was injected.

The administration completion data 500 may comprise a timestamp 510. The server 404 may use the timestamp 510 to determine compliance of the injection. The administration completion data 500 may further comprise a temperature data 512 as detected by the syringe 100. The temperature data 512 may aid in estimation of degradation of the pharmaceutical below the prescribed potency in the injectable.

By way of example, the administration completion data 500 may comprise a fraud, waste, and abuse data 518. The fraud, waste, and abuse data 518 may comprise an analog and/or digital force measurement as detected by a load sensor (described with respect to FIGS. 9A-9C). The server 404 may then determine whether an autoinjection was dispensed into the air (as a fraud, waste, and abuse rather than treatment). In alternative embodiments, the fraud, waste, and abuse data 518 may comprise a flag corresponding to whether the injection was legitimate or wasteful/fraudulent. In these embodiments, the microprocessor 210 may use the load sensor data to determine the flag. In these embodiments, the load sensor measurements may be compared to a predetermined force threshold, as injections into a patient may cause more resistance and corresponding higher force compared to a wasteful/fraudulent injection to the air. In some embodiments, a change in force (e.g. a delta) may be sensed and/or used to determine legitimacy of the injection. For example, an intradermal, intravenous, subcutaneous, or intramuscular injection may be detectable by corresponding predetermined force thresholds (ordered by lowest force to highest force threshold).

In some embodiments, the syringe 100 may be paired to a modem 410. The modem 410 may be substantially similar to wireless module 204. For example, the modem 410 may be in electronic communication with patient device 402, server 404, or the internet. The electronic communication connection may occur via ethernet, wireless, Bluetooth, cellular connection, etc. In this manner, the syringe 100 may not necessarily be connected directly to the server 404 or to cellular towers. Rather, these embodiments include the syringe 100 pairing to the modem 410 via modem connection 412. Modem connection 412 may be substantially similar in all respects to wireless connection 401. For example, modem connection 412 may allow electronic communication between the syringe 100 and the modem 410. Modem connection 412 may be wireless or wired, and may be Bluetooth, Bluetooth low energy, cellular, etc. In these embodiments, identifying information, such as the syringe Id 502, patient Id 504, potency 506, drug Id 514, etc. as stored on the syringe 100 may be set by the manufacturer, pharmacist, or other provider before receipt by the patient. Additionally, the syringe 100 may be set with a modem Id corresponding to the patient's modem 410 for verification of the patient's modem 410 with the particular syringe 100 and contained pharmaceutical. In some embodiments, the pharmacist or provider may update the patient's modem 410 with identifying information, such as syringe Id 502, patient Id 504, potency 506, drug Id 514, temperature data 512, treatment schedule 516, and/or fraud, waste, and abuse data 518. The identifying information of the syringe 100 may be compared to identifying information on the modem 410. If the identifying information matches, e.g. the patient Id 504 and drug Id 514 match between the syringe 100 and the modem 410, then the syringe 100 may establish electronic communication with the modem 410 to send the administration completion data 500 to the server 404 through modem 410. In this manner, modem 410 may comprise a cellular module and the syringe 100 and subsequent reporting syringes may connect to the modem 410 to send the administration completion data 500 to the modem 410, which may send the administration completion data 500 over the cellular connection. In some embodiments, establishing connection with modem 410 may also unlock syringe 100 to allow injection.

Figure 6:
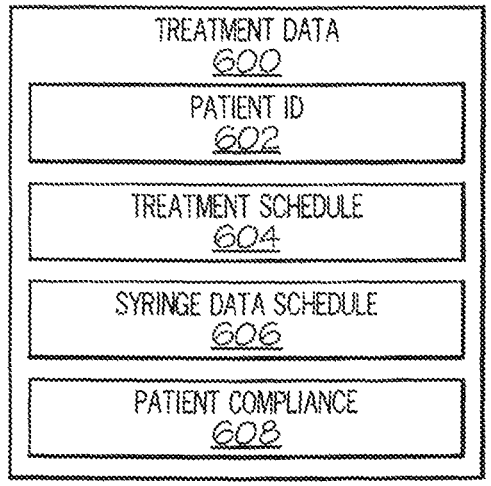
FIG. 6 depicts a block-level diagram of treatment data as can be stored on server of FIG. 4 in accordance with the principles of the present invention.

FIG. 6 depicts a block-level diagram of treatment data as can be stored on server 404 of FIG. 4 in accordance with the principles of the present invention. Treatment data 600 may be stored, collected, and/or calculated by the server 404. For example, treatment data 600 may correspond to a patient associated by a patient Id 602. A corresponding treatment schedule 604, as prescribed by physician 408b may be stored. The treatment schedule 604 may comprise prescribed potencies and prescribed injection timings. For example, the treatment schedule 604 may include the prescribed pharmaceuticals, corresponding potencies, and the injection regularity (e.g. daily, twice daily, etc.).

Syringe data schedule 606 may be stored and/or modified by the server 404. The syringe data schedule 606 may comprise the syringe data history received by the server 404 corresponding to the patient. For example, the syringe data schedule 606 may comprise the temperature of the pharmaceutical, the timestamp of administration, the potency, the administration completion flag, the syringe Id, the patient Id, the drug Id, etc.

Patient compliance 608 may be stored and/or calculated by the server 404. Patient compliance 608 may be determined by comparing the treatment schedule 604 to the syringe data schedule 606. If the syringe data schedule 606 is substantially similar in drug Id, potency, and injection timing to the treatment schedule 604, then patient compliance 608 may be set to reflect patient compliance. Otherwise, patient compliance 608 may be set to reflect patient non-compliance. In some embodiments, patient compliance 608 may be stored with regard to the full history of data recorded, by year, by month, by week, and/or by day.

Figure 7:
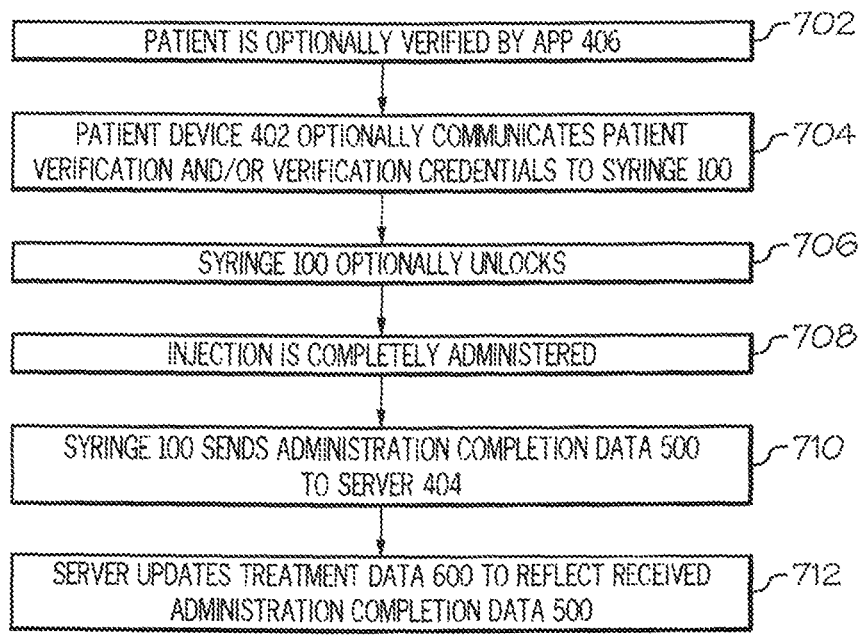
FIG. 7 depicts a block-level diagram of sending an administration completion data to the server in accordance with the principles of the present invention.

FIG. 7 depicts a block-level diagram of sending an administration completion data 500 to the server 404 in accordance with the principles of the present invention. In optional step 702, the patient may be verified by the app 406 on the patient device 402. Over wireless connection 401, the patient device 402 may indicate that the patient is verified and/or may send the patient verification data. The patient may be verified by username, password, patient Id, and/or digital certificate. In some embodiments, the patient may be verified by RSA key, fingerprint by sensor of patient device 402, and/or facial recognition by camera of patient device 402. Embodiments include two-factor verification, wherein two methods may be required to satisfy patient verification. For example, the app 406 may include a code or key that corresponds to the patient, but the patient must also provide fingerprint and/or facial verification through the patient device 402.

In optional step 704, the patient device 402 may communicate patient verification and/or verification credentials to the syringe 100. Later, the syringe 100 may unlock the locking mechanism 212 based on positive patient verification. In some embodiments, the microprocessor 210 may perform verification based on one or more of username, password, patient Id, face verification, retinal verification, vocal verification, fingerprint verification, and/or digital certificate. However, embodiments include receiving an indication of positive patient verification as performed by the app 406, patient device 402, and/or the server 404.

Upon verification, the syringe 100 may unlock the locking mechanism 212. In this manner the plunger 106 may be allowed to be compressed to administer the contained pharmaceutical.

In step 706, the syringe 100 may unlock, allowing for the administration of the drug in the barrel 102. However, embodiments include preventing the syringe 100 from unlocking when patient identification is not verified or when temperature data indicates that cold chain storage has been broken for the corresponding drug.

As described above, locking mechanism 212 may be reset from the locked position to the unlocked position in this step. By way of example, the microprocessor 210 may generate the administration completion data 500 corresponding to the current injection upon unlocking the syringe 100. The administration completion flag 508 may be set to False upon beginning administration of the injection. In some embodiments, the administration completion flag 508 may not necessarily be changed until the head 112 is fully compressed to the barrel 102. In this manner, partial injections may be reported. Thus, the microprocessor 210 may cause the administration completion data 500 to be sent to the server 404 after a predetermined elapsed time following unlocking the syringe 100 and/or load sensor detection, even if the sensor 206 does not indicate that injection has occurred.

In step 708, the injection may be completely administered to the patient. In this step, the head 112 may be substantially fully compressed when the injection is substantially completely administered. Magnet 114 may be sufficiently proximate the switch 206 such that the magnetic field may be detected. In this manner, an administration completion may be triggered. Alternatively, a mechanical switch may be pressed to trigger notification of administration completion. Therefore, an administration completion data 500 may be generated upon detection of the magnetic field, wherein the administration completion flag 508 reflects the completed injection (e.g. the administration completion flag 508 is set to True).

Administration completion may further trigger step 710, in which the syringe 100 may send the administration completion data 500 to the server 404. In step 712, the server 404 may update the treatment data 600 to reflect the received administration completion data 500.

Figure 11A:
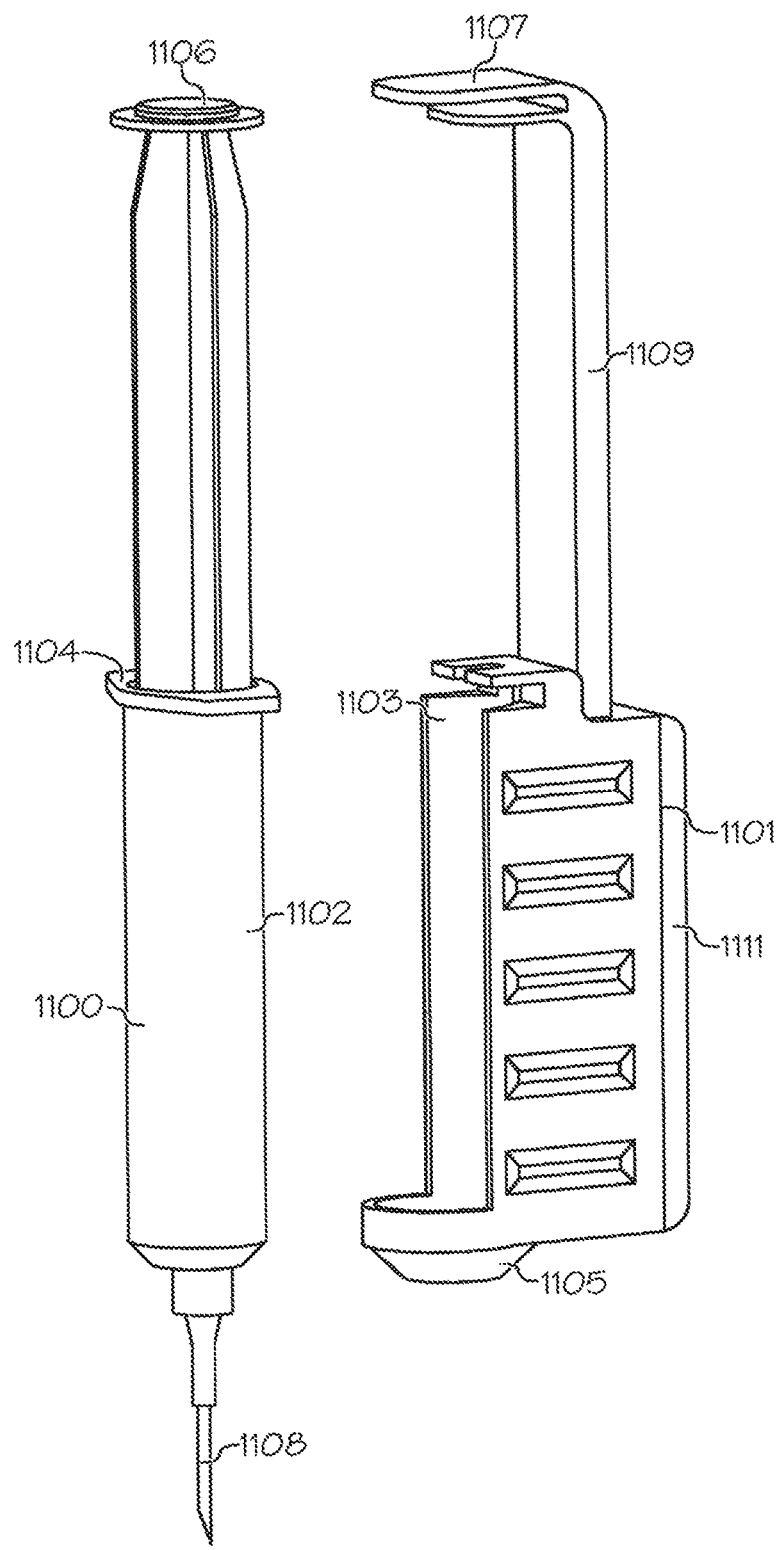
FIG. 11A depicts a diagram of an attachable reporting module in accordance with the principles of the present invention.

The method described with respect to FIG. 7 may also be performed with respect to an attachable reporting module, as depicted in FIG. 11A.

Figure 8:
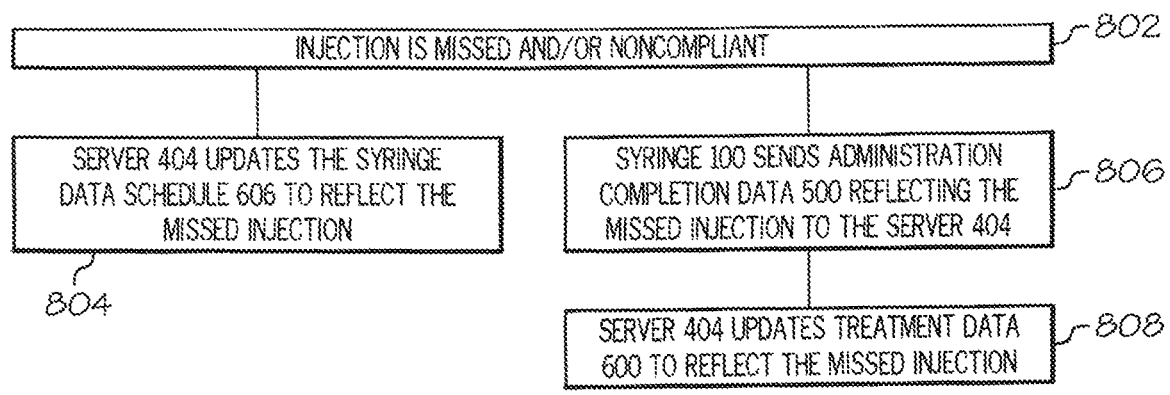
FIG. 8 depicts a block-level diagram of recording a missed injection in accordance with the principles of the present invention.

FIG. 8 depicts a block-level diagram of recording a missed injection in accordance with the principles of the present invention. In step 802, an injection may be missed based on a treatment schedule 516 and/or 604. In some embodiments, the treatment schedule 604 may be stored on the server 404, and the server 404 may automatically update the treatment data 600 to reflect the missed injection 804. In other embodiments, the treatment schedule 516 may be stored on the syringe 100, and the syringe may send the administration completion data 500 reflecting the missed injection to the server 404 in step 806. Step 806 may further comprise sending an administration completion data 500 reflecting an incomplete injection (e.g. administration completion flag 508 set to False) to the server 404 when an injection is non-compliant. A non-compliant injection can include an injection where administration was started, but not complete. Other non-compliant injections can include ejection of the drug from the syringe 100 without injecting into the patient, such as emptying the syringe 100 into air. In step 808, treatment data 600 may be updated to reflect the missed injection.

In some embodiments, the temperature sensor 202 may be used to record temperatures at a predetermined interval through the life cycle, such as transport, storage, etc., of the pharmaceutical. For example, the temperature sensor 202 could record temperatures daily, hourly, and/or every half-hour. In some instances, the temperature sensor 202 may record irregular temperatures, wherein the irregular temperature is known to risk degradation of the pharmaceutical. This temperature data 512 may be stored on the microprocessor 210 (e.g. temperature data 512). Upon sending the administration completion data 500, the sent administration completion data 500 may include life cycle data, such as the temperature history (e.g. temperature data 512).

The temperature data 512 may be used to determine whether the pharmaceutical remains potent and/or safe for injection, and subsequently, whether providers, pharmacists, insurers, and other stakeholders should rely on, use, or pay for that pharmaceutical. The temperature data 512 may comprise a temperature compliance flag that may be positive when the pharmaceutical remains within a predetermined threshold of temperatures for that pharmaceutical (e.g. cold chain storage), as detected by the temperature sensor 202. The temperature data 512 may comprise a temperature compliance flag. For example, the temperature compliance flag may default to True and may be changed to False upon detection of a freezing of the pharmaceutical by the temperature sensor 202. The temperature compliance flag may be changed to False upon elevation of the temperature above the predetermined temperature range threshold and/or temperature drop below the predetermine temperature range threshold. In some embodiments, the temperature data 512 and or temperature compliance flag may allow for a time tolerance for exceeding the predetermined temperature range (except that freezing is not allowed in some embodiments). In embodiments containing Humira, Enbrel, or Remicade, the temperature compliance flag may remain True unless the temperature of the drug is detected outside the range of 2 to 8 degrees Celsius. In some embodiments, the temperature compliance flag may not necessarily be changed until extended storage at room temperature is detected. In the embodiments of Humira and Enbrel, the temperature compliance flag may become False when the syringe 100 containing the drug is stored at room temperature for over 14 days. In embodiments having Remicade, the temperature compliance flag may become False when the syringe 100 is stored at room temperature for over 24 hours.

The predetermined temperature range thresholds may correspond to the particular pharmaceutical in the corresponding syringe 100. The predetermined temperature range thresholds may be set by a manufacturer, the pharmacist, an insurance provider, and/or a health care provider.

Some embodiments may include a temperature safety feature to prevent injection of degraded pharmaceuticals. For example, the locking mechanisms 212 may remain locked after the temperature compliance flag of temperature data 512 becomes False, regardless of verification of patient identification.

In some embodiments, the microprocessor 210 may be configured to calculate a degradation risk correlating to the pharmaceutical. In these embodiments, if the degradation risk is above a predetermined threshold, then the locking device 212 may prevent injection, even if the other criteria, such as patient verification, are satisfied. Additional embodiments include a timing circuit on the microprocessor 210. In some embodiments, the timing circuit may be used with the temperature sensor 202 to detect when the syringe 100 and/or pharmaceutical is removed from temperature controlled storage. The timing circuit may be used to ensure that the injection is made before a predetermined elapsed time. In these instances, the locking device 212 may prevent injection after the predetermined elapsed time from removal from storage, even if the other criteria are satisfied.

In some embodiments, the syringe 100 may be a multi-use system, wherein the syringe may be reusable and/or the reporting components 116 may be reusable. In these embodiments, the needle 104 may be replaceable and the reporting components 116 and/or administration completion data 500 may be reset upon changing the needle 104. Furthermore, the reporting components 116 and/or administration completion data 500 may be reset upon snap fit of the reporting components 116 to a new syringe 100. Resetting the reporting components 116 and/or administration completion data 500 may be triggered by a mechanical switch, such as when the mechanical switch is closed or opened. Changing the needle 104 and/or snap fitting the reporting components 116 to the syringe 100 may trigger the mechanical switch. However, many biologics may be provided as prefilled syringes 100 intended for single use administration. In these embodiments, the needle 104 may not necessarily be changed.

Figure 9A:
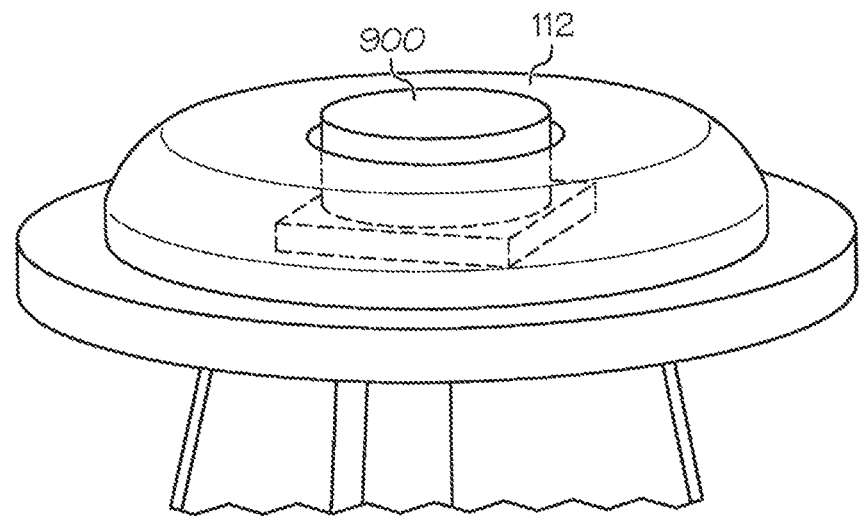
FIG. 9A depicts a diagram of a head of the reporting syringe comprising a load sensor in accordance with the principles of the present invention.
Figure 9B:
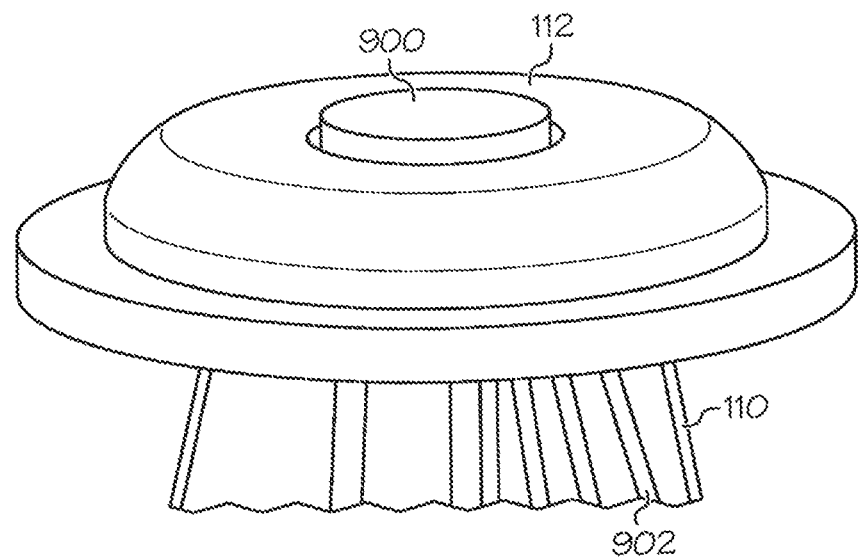
FIG. 9B depicts a diagram of a conductor of the reporting syringe in accordance with the principles of the present invention.
Figure 9C:
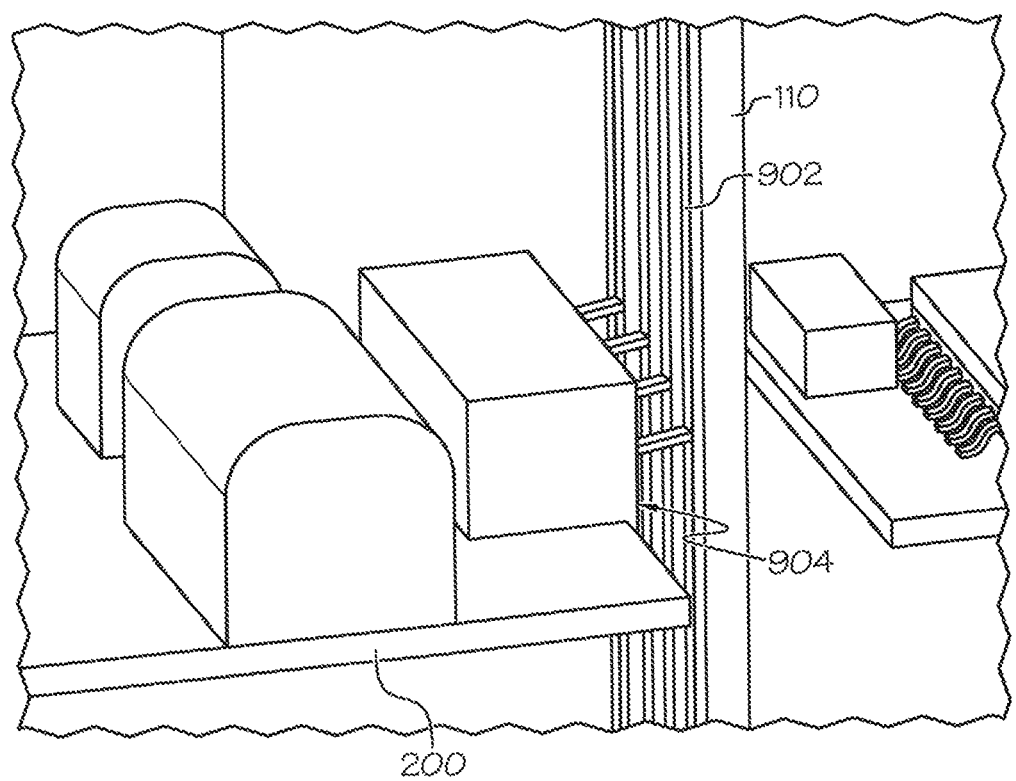
FIG. 9C depicts a diagram of the interaction of a stalk of the reporting syringe and a load sensor receiver in accordance with the principles of the present invention.

Additional embodiments of the syringe 100 may include a load sensor (described with respect to FIGS. 9A-9C). In these embodiments, the load sensor may be positioned on the needle proximate the barrel 102. In other embodiments, the load sensor may be positioned within the barrel 102 such that a pressure gradient in the syringe may be detected. The load sensor may be in electronic communication with the microprocessor 210 such that the load sensor may send detected pressure to the microprocessor 210. The microprocessor 210 may record and/or send the pressure data with the administration completion data 500. The load sensor may detect, for example, subcutaneous applied pressure, such as to determine that an intermuscular injection is occurring. In some embodiments, locking device 212 may prevent injection without the appropriate pressure detection by the load sensor. In other embodiments, the injection may be allowed, but administration completion data 500 may include a pressure data reflecting improper pressure detected. Embodiments also include the administration completion data 500 comprise pressure data, even with proper pressure detected.

The method described with respect to FIG. 8 may also be performed with respect to an attachable reporting module, as depicted in FIG. 11A.

FIG. 9A depicts a diagram of the head 112 of the reporting syringe 100 comprising a load sensor 900 in accordance with the principles of the present invention. The load sensor 900 may be present with or without the magnet 114. The load sensor 900 may comprise a force sensor. For example, some force sensors comprise a force-sensing resistor that comprises a material that changes resistance when a force, pressure, or mechanical stress is applied. Such materials may include a conductive polymer.

The changes in resistance may be interpolated to correspond to the force applied. In this manner, the force applied to inject the drug from the barrel 102 can be measured. This force may be higher when injecting into a patient, such as an intermuscular injection, rather than dispensing the drug through the needle without injection. By way of example, the additional force may result from mechanical resistance of the body of the patient to the injection compared to the relatively lower resistance when dispensing the drug into the air.

In these embodiments, a predetermined force threshold may be used to determine whether dispensing the drug resulted in a compliant injection or a non-compliant fraud, waste, and abuse. For example, measured force greater than the predetermined force threshold may correspond to a compliant administration of the drug. Furthermore, measured force less than the predetermined threshold may correspond to a wasteful or fraudulent occurrence, such as dispensing the drug into a sink.

Example force sensors may include the Honeywell FSA series, FSG series, FSS series, TBF series, or 1865 series. For example, the load sensor 900 may be able to measure from about 1 bar to about 10 bar, about 100 kPa to about 1 MPa, or about 15 psi to about 150 psi in pressure. The load sensor 900 may comprise millivolt analog output. Alternative embodiments may include other load cells that may be electronically read by the microprocessor.

FIG. 9B depicts a diagram of a conductor 902 of the reporting syringe in accordance with the principles of the present invention. The load sensor 900 may be in electrical and/or electronic communication with the conductor 902. The conductor 902 may comprise one or more electrically conductive traces and/or wires that run the length of the stalk 110. In this manner, the conductor 902 may remain in electrical communication with the circuit board 200 during the injection. Furthermore, the conductor 902 may allow the load sensor 900 to be in electrical communication with the circuit board 200 and/or the microprocessor 210 before, during, and/or after the injection. In embodiments wherein the load sensor 900 provides analog output, this output may be relayed to the microprocessor to be compared to the predetermined force threshold or converted to digital measurement and then compared to the predetermined threshold.

FIG. 9C depicts a diagram of the interaction of a stalk 110 of the reporting syringe 100 and a load sensor receiver 904 in accordance with the principles of the present invention. In some embodiments, the load sensor receiver 904 may be in electrical communication with the conductor 902 and/or the circuit board 200. In this manner, the load sensor receiver 904 may relay electrical and/or electronic signals and/or information from the conductor 902 to the microprocessor 210. In some embodiments, the load sensor receiver 904 may convert analog signals to digital signals. However, embodiments include a load sensor that may convert the analog signal to digital, in which the load sensor receiver 904 may relay the digital signal to the microprocessor 210. In other embodiments, the load sensor receiver 904 may relay the analog signal to the microprocessor 210 for conversion by the microprocessor, in embodiments wherein conversion is performed before comparison to the predetermined force threshold.

Figure 10A:
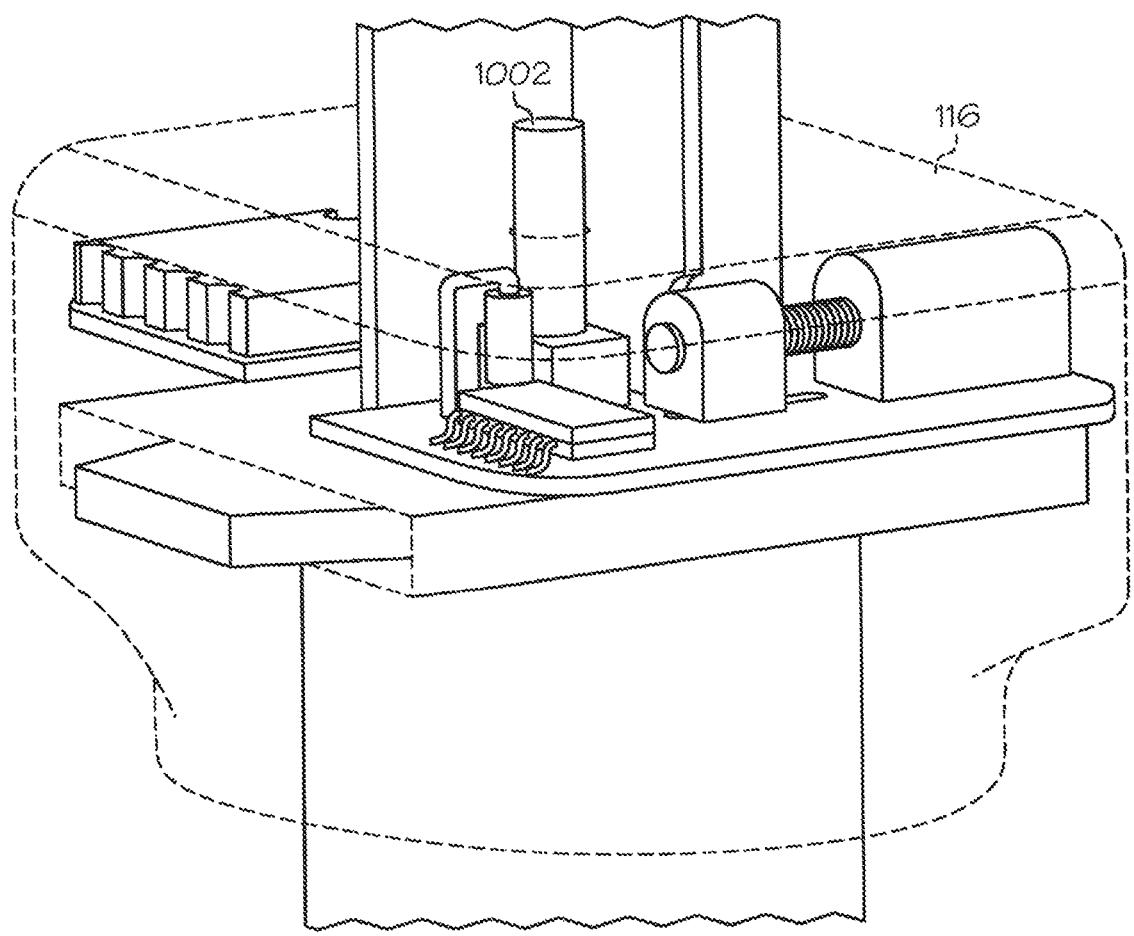
FIG. 10A depicts a diagram of a mechanical switch of the syringe of FIG. 1A in accordance with the principles of the present invention.

FIG. 10A depicts a diagram of a mechanical switch 1002 of the syringe 100 of FIG. 1A in accordance with the principles of the present invention. In these embodiments, the mechanical switch 1002 may optionally replace the switch 206. The mechanical switch 1002 may be in electrical communication with the reporting components 116 such that the administration completion data 500 may be sent upon pressing the mechanical switch 1002. The mechanical switch 1002 may comprise a resistance spring. The mechanical switch 1002 may further comprise a circuit. Upon pressing the mechanical switch 1002, the circuit may become opened or closed. The change in state of the circuit of the mechanical switch 1002 may trigger alteration and/or sending of the administration completion data 500.

Figure 10B:
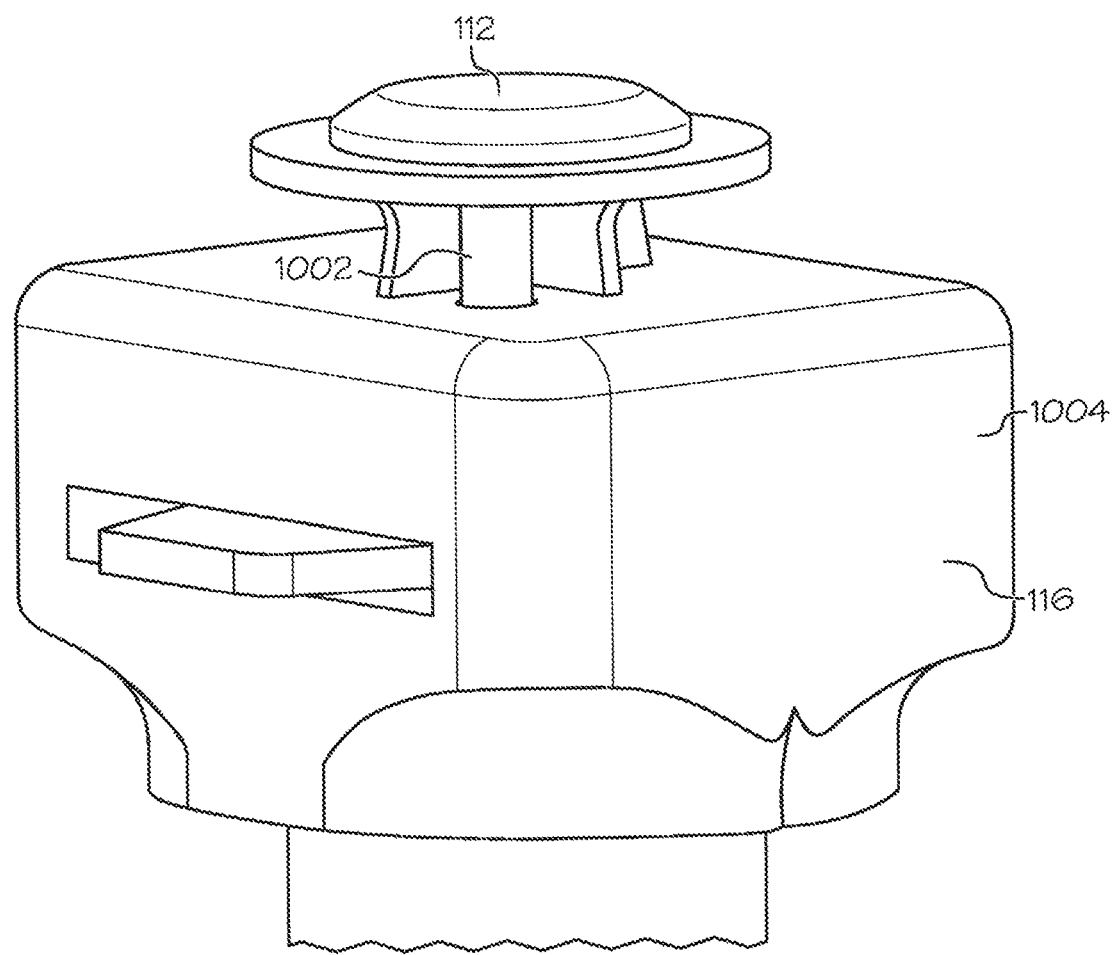
FIG. 10B depicts a diagram of an alternative view of the mechanical switch of FIG. 10A in accordance with the principles of the present invention.

FIG. 10B depicts a diagram of an alternative view of the mechanical switch 1002 of FIG. 10A in accordance with the principles of the present invention. FIG. 10B depicts that the mechanical switch 1002 may extend beyond a housing 1004 of the reporting components 116. In these embodiments, the head 112 may not necessarily comprise a magnet. Rather, the head 112 may press the mechanical switch 1002 upon injection completion (e.g. when the head 112 is pressed to the housing 1004).

Figure 10C:
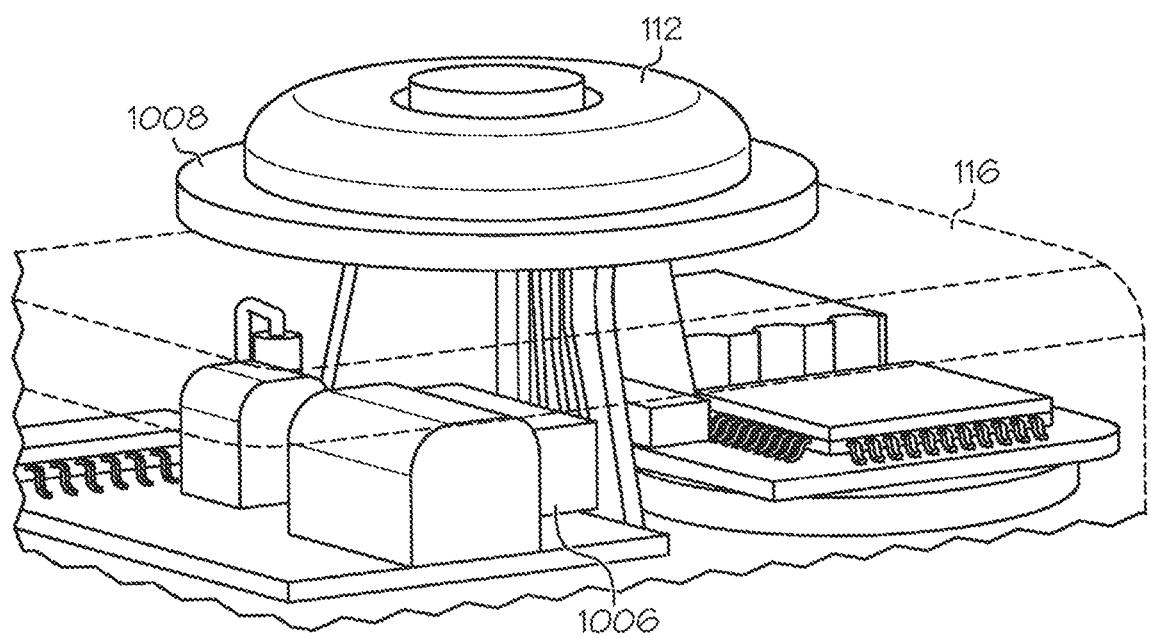
FIG. 10C depicts a diagram of another alternative view of the mechanical switch of FIG. 10A in accordance with the principles of the present invention.

FIG. 10C depicts a diagram of another alternative view of the mechanical switch 1002 of FIG. 10A in accordance with the principles of the present invention. The head 112 may comprise a stamping 1008 that may press the mechanical switch 1002 when fully pressed. The mechanical switch 1002 may comprise a mechanical switch contact 1006 that may be in electrical and/or electronic communication with the reporting components 116. Upon pressing the mechanical switch 1002, the reporting components 116 may generate or alter the administration completion data 500. Upon pressing the mechanical switch 1002, the reporting components 116 may send the administration completion data 500.

FIG. 11A depicts a diagram of an attachable reporting module 1101 in accordance with the principles of the present invention. The reporting module 1101 may be attachable and/or detachable from a standard syringe 1100. For example, the reporting module 1101 may comprise a barrel receiver 1105, a grip receiver 1103, and/or a head receiver 1107. The reporting module 1101 may further comprise a slide 1109 such that the head receiver 1107 may be pressed with a head 1106 of the syringe 1100. These structures may allow the reporting module 1101 to be attached to the standard syringe 1100 by frictional engagement. For example, a barrel 1102 of the syringe 1100 may be received in the barrel receiver 1105. The barrel receiver 1105 may comprise a conical or frusto-conical shape configured to receive and/or frictionally engaged the barrel 1102 proximate a needle 1108.

The grip receiver 1103 may be configured to receive and/or frictionally engage a grip 1104 of the syringe 1108. The grip receiver 1103 may be positioned the length of the barrel 1102 from the barrel receiver 1105. The grip 1104 may comprise flat flanges extending orthogonally from an end of the barrel 1102. The grip receiver 1103 may comprise a first support and a second support set apart at a sufficient distance to frictionally engage the flanges of the grip 1104 when inserted.

Furthermore, the head receiver 1107 may be in slideable communication with a base 1111 of the reporting module 1101 via slide 1109. In this manner, the head receiver 1107 may rest against and/or frictionally engage the head 1106 such that pressing the head receiver 1107 may press the head 1106 thereby administering an injection. Head receiver 1107 may comprise a single projection orthogonal to the slide 1109. Alternative embodiments include a first projection and a second projection. The first projection and second projection may be spaced apart such that the first projection may engage a distal side of the head 1106. The second projection may be distance sufficiently to engage a proximate side of the head 1106. In some embodiments, the second projection may frictionally fit against a feature, such as a stamping of the head 1106.

Figure 11B:
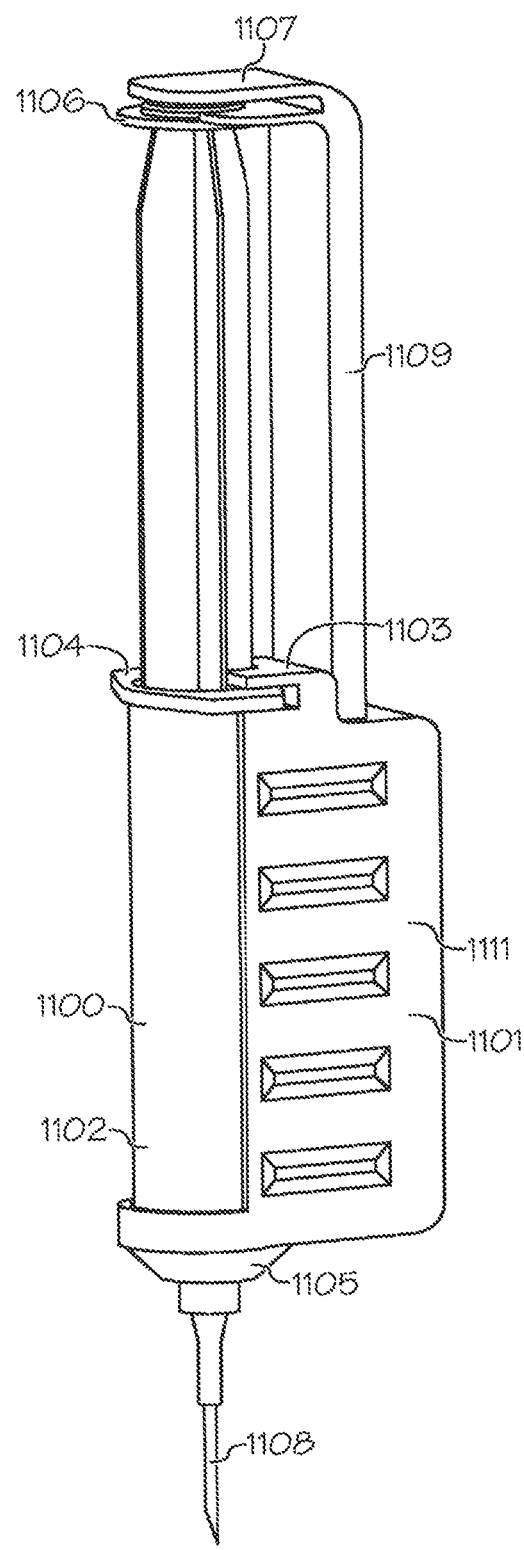
FIG. 11B depicts a diagram of the reporting module of FIG. 11A attached to a standard syringe in accordance with the principles of the present invention.

FIG. 11B depicts a diagram of the reporting module 1101 of FIG. 11A attached to a standard syringe 1101 in accordance with the principles of the present invention. As depicted, the syringe 1101 may be frictionally engaged with the reporting module 1101. In some embodiments, the second projection of the head receiver 1107 may frictionally engage one or more features of the head 1106, such as the stamping.

Figure 11C:
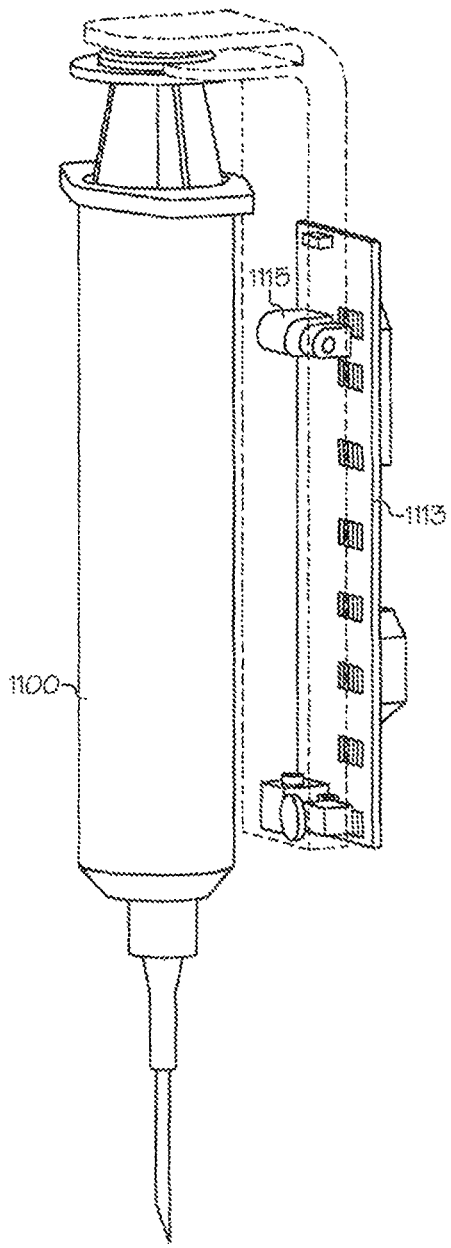
FIG. 11C depicts a diagram of the reporting components of the reporting module of FIG. 11B in accordance with the principles of the present invention.

FIG. 11C depicts a diagram of the reporting components 1113 of the reporting module 1101 of FIG. 11B in accordance with the principles of the present invention. In some embodiments, the reporting components 1113 may be substantially similar to the reporting components 116. By way of example, the reporting components 1113 may comprise one or more of a temperature sensor, a wireless module, a switch, a battery, a microprocessor, a locking mechanism, etc. Furthermore, the components may be in electrical and/or electronic communication with one another, such a via a circuit board. For example, locking mechanism 1115 may comprise a mortise formed in the slide 1109 that may receive a tenon of the locking mechanism 1115 to prevent injection when the reporting module 1101 is engaged to the syringe 1100.

Figure 11D:
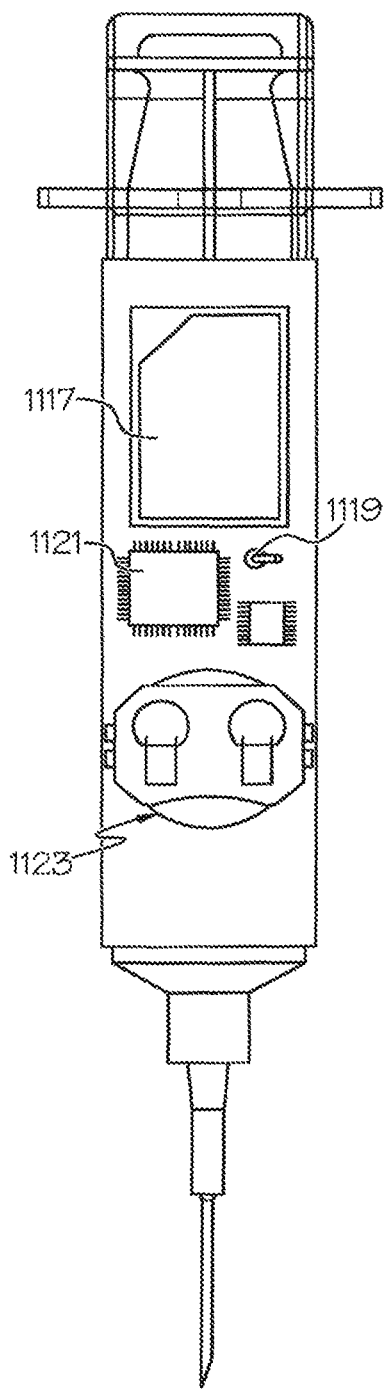
FIG. 11D depicts an alternative view of the reporting components of FIG. 11C in accordance with the principles of the present invention.

FIG. 11D depicts an alternative view of the reporting components of FIG. 11C in accordance with the principles of the present invention. The reporting components 1113 may comprise a wireless module 1117, a temperature sensor 1119, a microprocessor 1121, and/or a battery 1123. These components may be substantially similar to the corresponding components of reporting syringe 100.

Figure 11E:
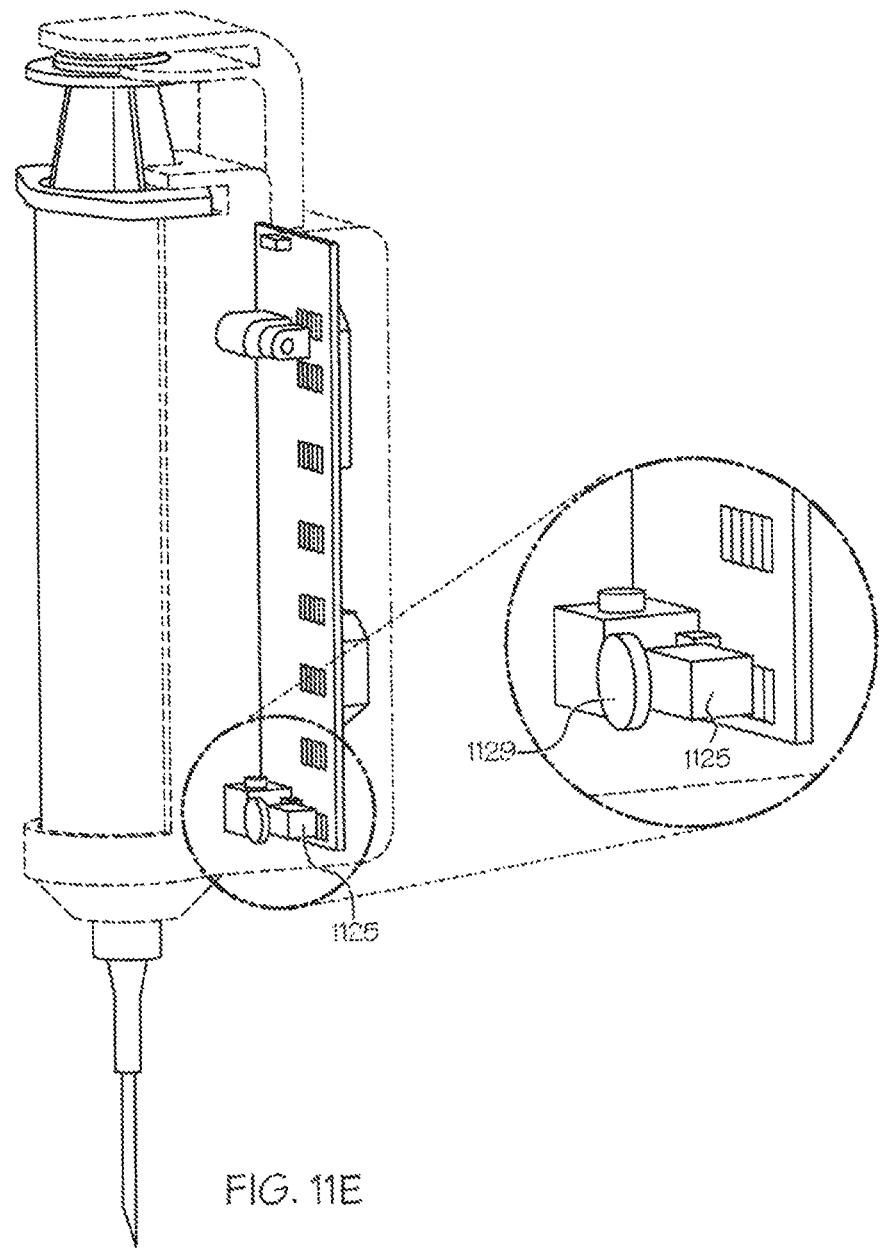
FIG. 11E depicts an internal view of the reporting components of FIG. 11C in accordance with the principles of the present invention.

FIG. 11E depicts an internal view of the reporting components of FIG. 11C in accordance with the principles of the present invention. The reporting components 1113 may comprise a switch 1125. The switch 1125 may comprise any structure sufficient for generating an electrical signal to the processor upon triggering the switch 1125. The switch 1125 may comprise a mechanical switch that is substantially similar to mechanical switch 1002. In other embodiments, the switch 1125 may comprise an electronic switch that is substantially similar to switch 206. In some embodiments, the switch 206 may comprise the mechanical switch 1002. In embodiments wherein the switch 1125 comprises a Reed switch, the slide 1109 may comprise a magnet positioned to trigger the switch 1125 when fully pressed.

Figure 11F:
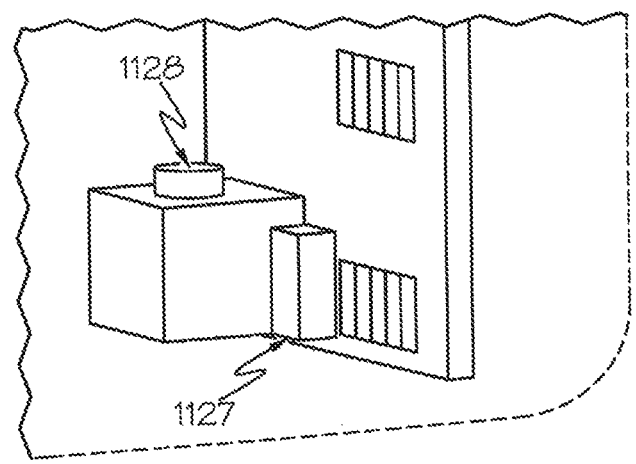
FIG. 11F depicts a zoomed view of the reporting components of FIG. 11C in accordance with the principles of the present invention.

FIG. 11F depicts a zoomed view of the reporting components 1113 of FIG. 11C in accordance with the principles of the present invention. In some embodiments, the switch 1125 may comprise a Reed switch 1127 and a magnet 1129. The magnet 1129 may induce a magnetic field to trigger the Reed switch 1127 when the slide 1109 is compressed. The switch 1125 may comprise a microswitch 1128. A microswitch 1128 may comprise a miniature snap-action switch. The microswitch may comprise an electric switch that may be actuated by relatively low physical force, such as through the use of a tipping-point mechanism or an "over-center" mechanism.

Figure 11G:
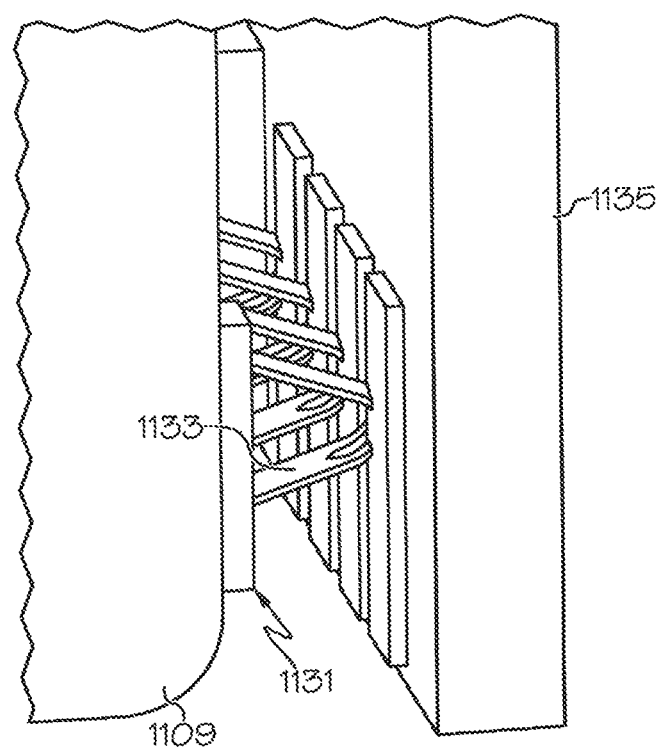
FIG. 11G depicts an alternate zoomed view of the reporting components of FIG. 11C in accordance with the principles of the present invention.

FIG. 11G depicts an alternate zoomed view of the reporting components 1113 of FIG. 11C in accordance with the principles of the present invention. In some embodiments, the switch 1125 may comprise a mechanical switch 1131. The mechanical switch 1131 may comprise one or more spring-loaded PCB (printed circuit board) contacts. When the slide 1109 is compressed, the spring-loaded PCB contacts 1133 may be pressed to open or close a circuit. The action of the spring-loaded PCB contacts may trigger generation and/or sending the administration completion data 500. A circuit board 1135 of the reporting components 1113 may comprise pressure sensitive spring-loaded PCB contacts. In some embodiments, the circuit board 1135 may simply comprise contacts and the slide 1109 may comprise the spring-loaded contacts that provide electrical communication to trigger generating and/or sending the administration completion data 500 when the spring-loaded contacts are aligned with the circuit board contacts.

In some embodiments, the switch 1125, such as the spring-loaded PCB contacts, may reset the administration completion data 500. In this manner, the spring-loaded PCB or other mechanical switch may be pressed when attaching the reporting module 1101 to a new syringe 1100.

The previous description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with each claim's language, wherein reference to an element in the singular is not intended to mean "one and only one" unless specifically so stated, but rather "one or more." All structural and functional equivalents to the elements of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

What is claimed is:

1. A syringe, comprising:
   a barrel in fluid communication with a needle connected with a first end of the barrel;
   a piston comprising a plunger, the piston positioned within a second end of the barrel and the plunger having a fluid-tight interaction with the interior of the barrel; and
   a microprocessor in electronic communication with a temperature sensor and a locking mechanism engaged with a stalk of the piston to prevent injection,
   wherein the locking mechanism is configured to unlock upon electronic patient verification by the microprocessor unless a temperature data, corresponding to temperatures detected by the temperature sensor, comprises temperatures outside a predetermined temperature range for longer than a predetermined time tolerance.

2. The syringe of claim 1, wherein the predetermined temperature range is 2 to 8 degrees Celsius and the time tolerance is 14 days, and wherein the predetermined temperature range excludes freezing.

* * * * *